US006918698B2

(12) United States Patent
Nordmeyer et al.

(10) Patent No.: US 6,918,698 B2
(45) Date of Patent: Jul. 19, 2005

(54) INTEGRATED CRYSTAL MOUNTING AND ALIGNMENT SYSTEM FOR HIGH-THROUGHPUT BIOLOGICAL CRYSTALLOGRAPHY

(75) Inventors: Robert A. Nordmeyer, San Leandro, CA (US); Gyorgy P. Snell, Richmond, CA (US); Earl W. Cornell, Antioch, CA (US); William Kolbe, Moraga, CA (US); Derek Yegian, Oakland, CA (US); Thomas N. Earnest, Berkeley, CA (US); Joseph M. Jaklevic, Lafayette, CA (US); Carl W. Cork, Walnut Creek, CA (US); Bernard D. Santarsiero, Chicago, IL (US); Raymond C. Stevens, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 24 days.

(21) Appl. No.: 10/319,282

(22) Filed: Dec. 12, 2002

(65) Prior Publication Data

US 2003/0152194 A1 Aug. 14, 2003

Related U.S. Application Data

(60) Provisional application No. 60/341,020, filed on Dec. 12, 2001.

(51) Int. Cl.[7] .............................................. G01N 23/00
(52) U.S. Cl. ...................................... 378/205; 378/79
(58) Field of Search ............................... 378/71, 73, 74, 378/79, 80, 81, 205, 206, 208, 68, 69; 250/440.11, 442.11, 491.1

(56) References Cited

U.S. PATENT DOCUMENTS

| | | | |
|---|---|---|---|
| 3,992,624 A | * | 11/1976 | Flannery et al. ............... 378/74 |
| 5,359,640 A | | 10/1994 | Fink et al. |
| 5,727,043 A | * | 3/1998 | Watanabe .................... 378/109 |
| 6,064,717 A | | 5/2000 | Ortega et al. |
| 6,249,566 B1 | | 6/2001 | Hayashi et al. |
| 6,385,289 B1 | | 5/2002 | Kikuchi |
| 6,404,849 B1 | | 6/2002 | Olson et al. |
| 6,408,047 B1 | | 6/2002 | Kitagawa et al. |
| 6,621,085 B1 | * | 9/2003 | Cipriani et al. ......... 250/442.11 |

FOREIGN PATENT DOCUMENTS

| | | | | |
|---|---|---|---|---|
| WO | WO 200040952 A2 | * | 7/2000 | ............ G01N/1/28 |
| WO | WO 01/11345 A2 | | 2/2001 | |
| WO | WO 02/29395 A1 | | 4/2002 | |

OTHER PUBLICATIONS

"Product Information," The Rigaku Journal, vol. 16 (No. 2), p. 1–7, (1999).

* cited by examiner

*Primary Examiner*—Edward J. Glick
*Assistant Examiner*—Chih-Cheng Glen Kao
(74) *Attorney, Agent, or Firm*—Joseph R. Milner

(57) ABSTRACT

A method and apparatus for the transportation, remote and unattended mounting, and visual alignment and monitoring of protein crystals for synchrotron generated x-ray diffraction analysis. The protein samples are maintained at liquid nitrogen temperatures at all times: during shipment, before mounting, mounting, alignment, data acquisition and following removal. The samples must additionally be stably aligned to within a few microns at a point in space. The ability to accurately perform these tasks remotely and automatically leads to a significant increase in sample throughput and reliability for high-volume protein characterization efforts. Since the protein samples are placed in a shipping-compatible layered stack of sample cassettes each holding many samples, a large number of samples can be shipped in a single cryogenic shipping container.

6 Claims, 16 Drawing Sheets

FIG. 2A
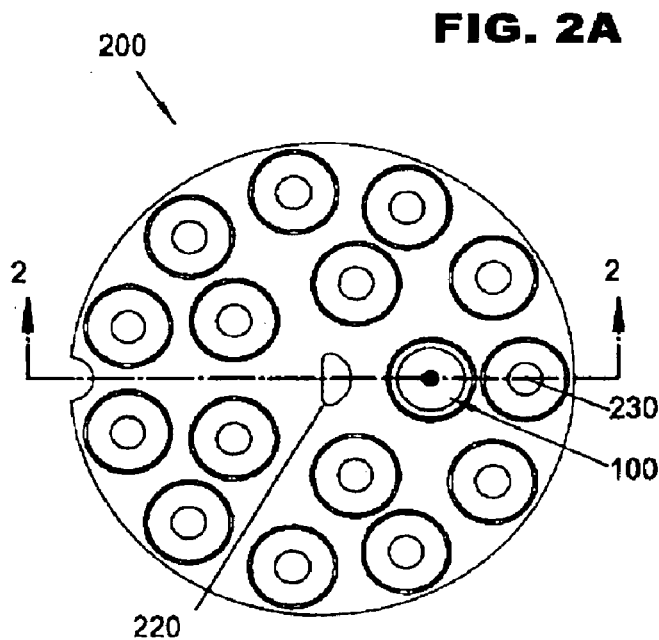
FIG. 2B
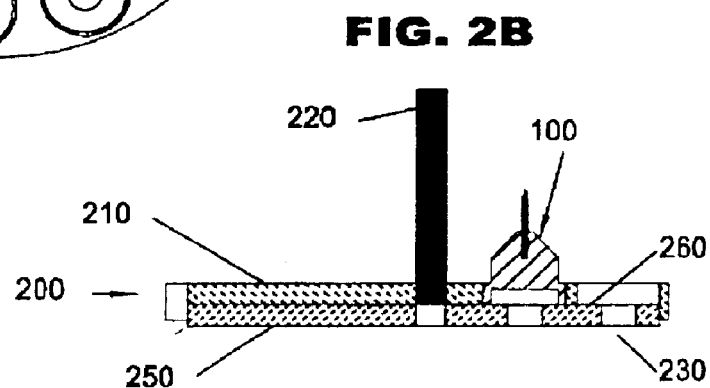
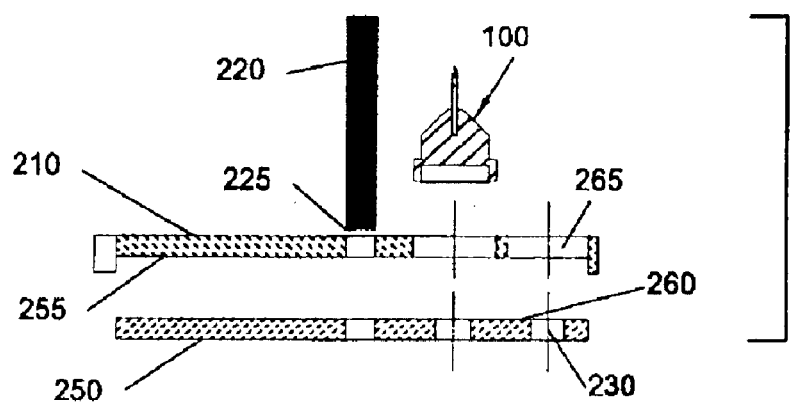
FIG. 2C

FIG. 5A
FIG. 5B
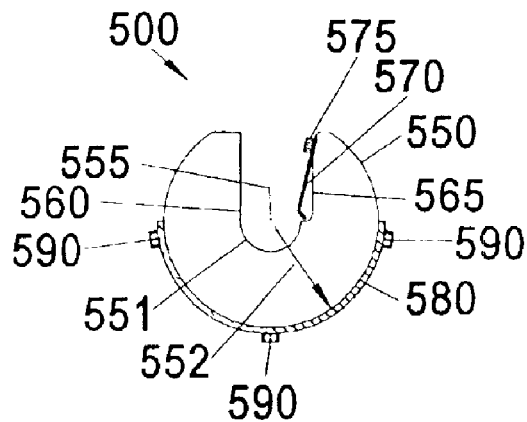
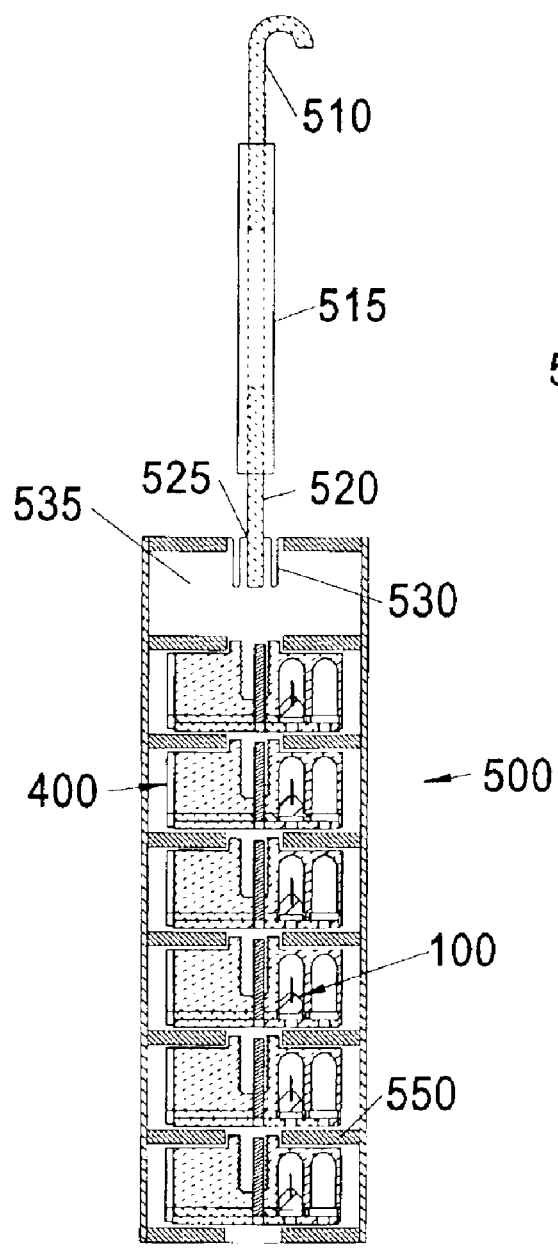

SECTION 7-7

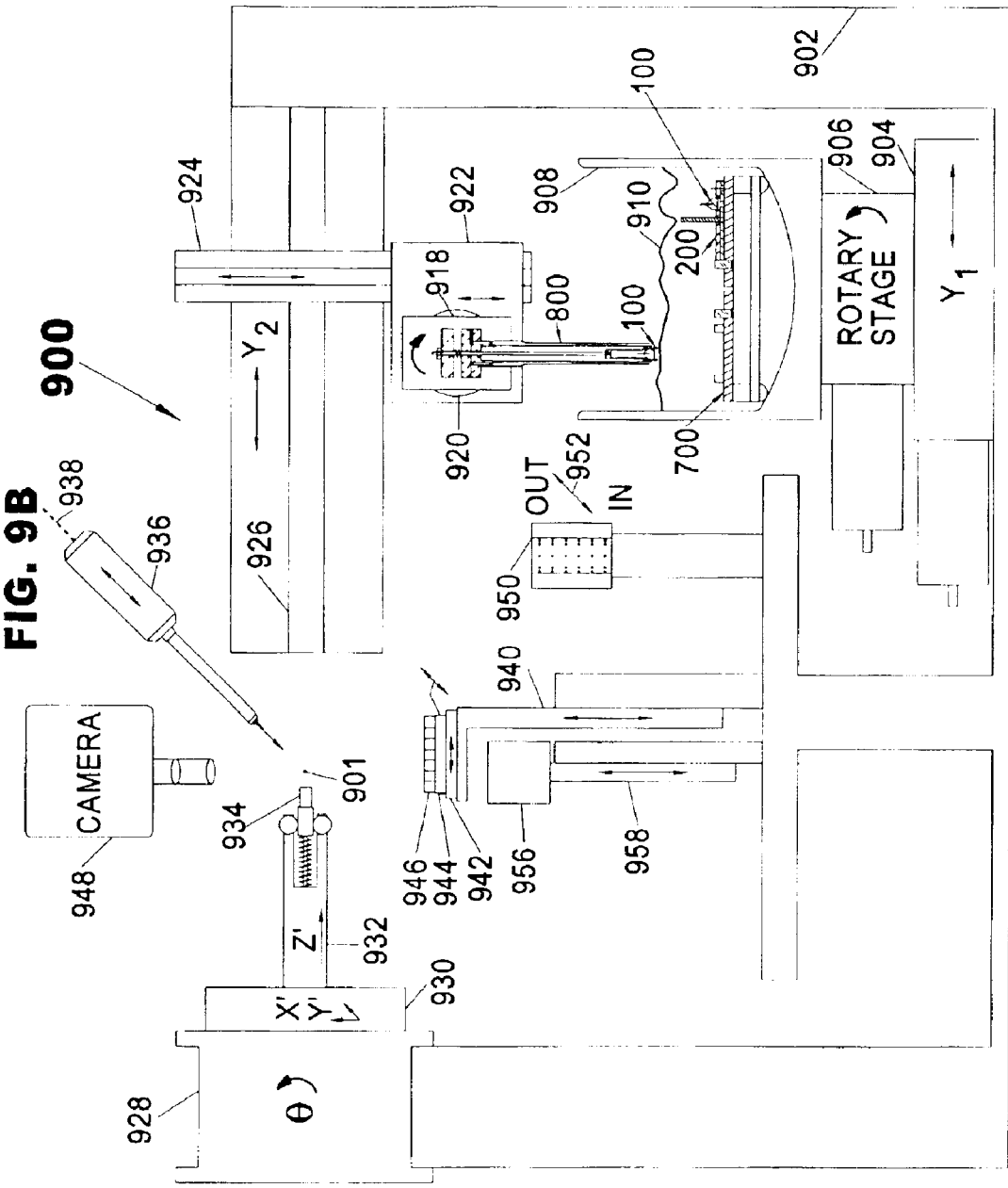

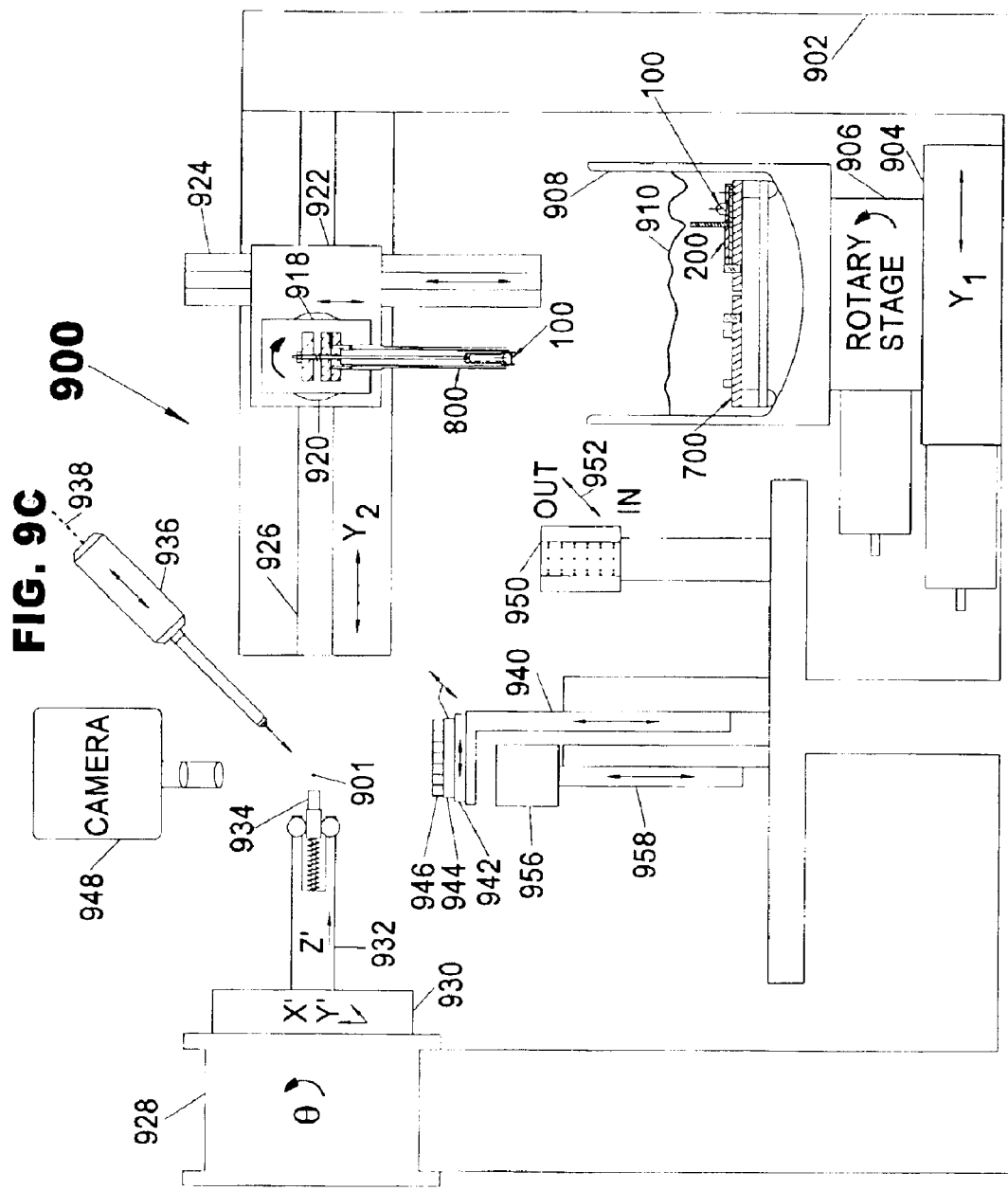

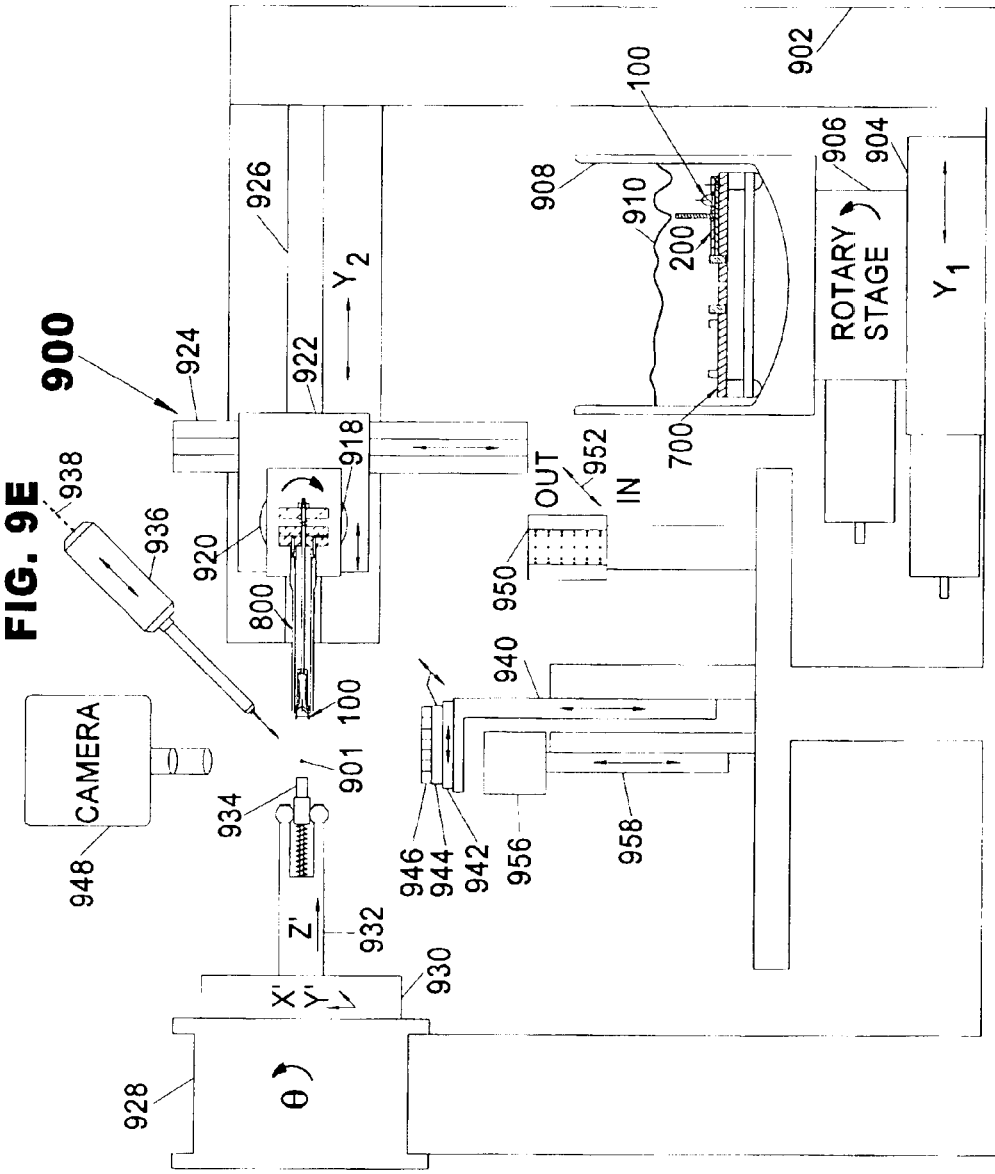

US 6,918,698 B2

INTEGRATED CRYSTAL MOUNTING AND ALIGNMENT SYSTEM FOR HIGH-THROUGHPUT BIOLOGICAL CRYSTALLOGRAPHY

CROSS REFERENCE TO RELATED APPLICATIONS

This application claims benefit of U.S. Provisional Patent Application No. 60/341,020, filed on Dec. 12, 2001, and entitled "Integrated Crystal Mounting and Alignment System for High-throughput Biological Crystallography", which is hereby incorporated by reference in its entirety.

STATEMENT REGARDING FEDERAL FUNDING

This invention was made with U.S. Government support under Contract Number DE-AC03-76SF00098 between the U.S. Department of Energy and The Regents of the University of California for the management and operation of the Lawrence Berkeley National Laboratory. The U.S. Government has certain rights in this invention.

REFERENCE TO A COMPUTER PROGRAM

Not applicable.

BACKGROUND OF THE INVENTION

1. Field of the Invention

The present invention generally relates to the transportation, robotic crystal mounting and alignment, manipulation, mounting, alignment of crystal samples in a variety of experimental environments. The present invention more particularly relates to the mounting, alignment, and exposure of samples to synchrotron radiation for high-speed x-ray crystallography.

2. Description of the Relevant Art

Overview of X-ray Crystallographic Systems

Aspects of the present invention facilitate the transportation, as well as the remote and unattended mounting and alignment of frozen crystals—of e.g. biological materials, such as proteins, lipids, or deoxyribonucleic acids (DNA)—for x-ray diffraction analysis. A major challenge in the x-ray diffraction analysis system design is the necessity of storing the samples in liquid nitrogen before mounting and following removal, as well as maintaining the samples at near liquid nitrogen temperature throughout the mounting, alignment, and x-ray diffraction analysis data acquisition process. Additionally, the precision and stability of the crystal sample location alignment must be very high, with absolute sample position maintained within a few microns while rotating in one axis while being exposed to an incident x-ray beam through as much as a full 360°.

Traditional x-ray diffraction analysis crystal sample handling procedures are operator-intensive, requiring continuous manual operator intervention at the measurement station. The ability to perform these tasks remotely and automatically significantly increases crystal mounting and measurement throughput, as well as reliability for large-scale protein crystallography characterization. An increase in throughput multiplies the number of samples that may be analyzed in a given time period, thus decreasing the time per sample, thereby lowering the cost associated with synchrotron-based x-ray crystallography.

Synchrotron-Based X-ray Crystallography

One embodiment of this invention is in the area of cryogenic protein crystallography at synchrotron sources, although the robotic mounting and alignment system can be adapted for other laboratory x-ray sources. Potential uses include high-volume protein characterization experiments. The level of application of this invention could range from a small experimental program processing only a few samples per day to large projects screening and analyzing many thousands of samples per year.

Synchrotron-based x-ray crystallography is one application of this invention. Synchrotrons are capable of producing intense monochromatic pseudo-coherent photons of precisely controllable energies. The property of high intensity (otherwise known as high brightness) of the synchrotron x-ray beams means that acquisition of crystal lattice diffraction patterns can be done very rapidly, whereas other, lower intensity beams may require several times longer for a diffraction pattern to be acquired. The high brightness of the synchrotron radiation, combined with the narrow energy bandwidth achievable using a monochromator, can lead to exceedingly high-resolution x-ray diffraction patterns.

The x-ray diffraction patterns can subsequently be analyzed to infer the relative spatial positions of the atoms constituting the crystal lattice structure. The overall x-ray diffraction analysis of crystals is known as x-ray crystallography. The information contained in the crystal structure can lead to important insights about the function of the molecule and into molecular-chemical interactions. Such insights can lead to targeted, and thus faster, pharmaceutical development and improved pharmaceuticals: a field known as 'structure based pharmaceutical design'.

Biological Crystallography Mounting Techniques

Currently, most x-ray crystallography work is done using synchrotron x-ray sources. These x-ray sources are extremely expensive to operate, which means that time is precious. However, since synchrotron x-ray crystallography is still a recent phenomenon, most sample mounting is done manually, which is both slow and imprecise. Furthermore, since crystallography must be done on crystalline material, the sample must be maintained in a frozen state. Typically, this is ensured by keeping the sample at near liquid nitrogen temperatures.

The requirement that the sample be maintained at liquid nitrogen temperature, however, requires that technicians and scientists can only mount the samples using cumbersome techniques of indirectly handling the sample. Thus, people cannot be allowed to inadvertently heat the sample, and reciprocally, the sample handling tools, and sample handling fixtures, cannot freeze the fingers of the people who do the mounting. To meet this requirement, clumsy tools resembling forceps or pliers are used. These tools are somewhat cumbersome, further adding time and difficulty in mounting and handling the sample.

As more time is required to manually mount the sample, more heat is transferred from the ambient atmosphere, raising the crystal sample temperature. Some biological crystal samples, frozen at a critical point in a chemical reaction with another compound, continue their reactions at temperatures as low at 100° K., only about 22° K. above that of liquid nitrogen. This stringent maximum temperature requirement for some samples implies that the sample must be actively cooled during the entire mounting process, which adds still further time and complexity to the mounting process. It is preferable that the sample crystals be cooled to a temperature not in excess of 150° K., more preferably not in excess of 130° K., yet more preferably not in excess of 110° K., still more preferably not in excess of 100° K., yet still more preferably not in excess of 90° K., and most preferably not in excess of 80° K.

The largest time-related issue with manual operator mounting of synchrotron x-ray crystallography samples is that the humans must enter the x-ray irradiation area ('the hutch') to mount and dismount the crystal samples. This action involves in turn a sequence of safety interlocking steps to protect the personnel from a harmful and potentially lethal dosage of x-rays used to irradiate the crystal sample to generate the diffraction patterns. Typically, one or more heavy lead-lined doors must be opened and closed, additional beam shutters inserted, and interlocking safety devices must be carefully verified for safe operation, prior to human access to the sample.

The result is that manual mounting of a synchrotron x-ray crystallography sample is slow. As a result of being slow, manual mounting is very expensive as measured in synchrotron beam time.

Biological Crystallography Sample Transportation

Currently, there are relatively few synchrotron x-ray sources available for x-ray crystallography. Therefore, scientists wishing to use synchrotron x-ray sources face the dilemma of transporting the crystal samples to the synchrotron while simultaneously maintaining the crystal's cryogenically frozen state.

A particularly fruitful use of synchrotron x-ray crystallography is in detection of chemical interactions within a specific biological sample. These interactions are evanescent in nature, sometimes reacting in the one-nanosecond time scale. Additionally, typical biological processes can follow a number of biochemical pathways that are time dependent. Some of these biochemical pathways proceed even at temperatures as low as 100° K. Thus, for a scientist to determine the crystalline structure of an intermediate state biochemical interaction, the biological sample must be frozen to a temperature low enough to inhibit further reaction, typically close to the liquid nitrogen temperature of about 77° K. under normal laboratory conditions.

A Relevant Patent

Abbott Laboratories is the named assignee of U.S. Pat. No. 6,404,849 B1 (the '849 patent), entitled "Automated Sample Handling for X-Ray Crystallography". The '849 patent discloses algorithms for centering a crystal at a reference position relative to home position sensors, as well as the hardware for screwing a threaded sample holding device on and off a positioning device. The '849 patent uses a multi-axis robot to move crystals from a sample rack to a positioning device.

SUMMARY OF THE INVENTION

One aspect of the present invention is directed toward the transportation and manipulation of samples of cryogenically frozen biological particles, preferably protein crystals, mounted on standardized base-pin configured sample assemblies.

The integrated crystal mounting and alignment system for high-throughput biological crystallography which transports and manipulates the sample assemblies comprises eight major components:

1) a sample repository having a storage Dewar filled with liquid nitrogen, capable of keeping many samples cryogenically frozen, with a sample repository stage able to addressably move the sample assemblies to a point where a particular sample assembly can be extracted;
2) a system for shipping, storing and handling of the sample assemblies at cryogenic temperatures, preferably liquid nitrogen temperatures;
3) a computer-controlled sampling system sequencing a particular sample assembly through the steps of: a) selecting the particular sample assembly from the cryogenic sample repository, b) removing the selected sample assembly from the sample repository, c) transferring the sample assembly to a three axis positioner mounted on a goniometer head, d) centering the sample in the x-ray beam, e) exposing the sample (held by the mounted sample assembly) to x-ray radiation to produce a crystallographic image at a sequence of rotational exposure angles while simultaneously maintaining the sample's cryogenic temperatures, and f) replacing the sample assembly back in the cryogenic sample repository;
4) a sample gripper capable of firmly grasping a sample assembly, while keeping the sample at cryogenic temperature;
5) a gripper stage, using the sample gripper to: remove the sample assembly from cryogenic sample repository, transport the sample to a sample positioner, and replace the sample assembly in the sample repository, while at all times maintaining the temperature of the sample at or below 78° K.;
6) a sample gripper defroster capable of keeping the sample gripper free of frost buildup during cycles of sample assembly mounting and dismounting (or unmounting) in ambient humid air;
7) a sample positioner consisting of a precision three-axis positioner mounted on a precision goniometer; and
8) an optical alignment system that provides feedback to the sample positioner for precise alignment of the sample to a predefined point in space within the x-ray beam during sample rotation.

BRIEF DESCRIPTION OF THE DRAWINGS

FIG. 2A is a top view of a sample cassette with one sample assembly.

FIG. 2B is a cross sectional view through section 2—2 of FIG. 2A of a sample cassette with one sample assembly.

FIG. 2C is an exploded view of the cross sectional view of FIG. 2B, with a sample cassette with one sample assembly.

FIG. 5A is a cross sectional view of a sample cassette carrier with six assembled sample cassettes present and the top slot vacant.

FIG. 5B is a bottom view of the sample cassette carrier and all assembled sample cassettes absent.

FIG. 9B is a partial front view of the integrated robotic crystal mounting and alignment system showing most of the major subsystems, where the system has retracted a pneumatic stage, known as SmallMove, causing the sample gripper to move vertically upwards.

FIG. 9C is a partial front view of the integrated robotic crystal mounting and alignment system showing most of the major subsystems, where the system has retracted the transverse vertical stage, known as UpDown, causing the sample gripper to move further vertically upwards.

FIG. 9E is a partial front view of the integrated robotic crystal mounting and alignment system showing most of the major subsystems, where the horizontal stage has moved the sample gripper in a long horizontal translation, causing the sample gripper to move to a predetermined distance toward the sample positioner.

DETAILED DESCRIPTION OF THE PREFERRED EMBODIMENT

Definitions

Figure 1:
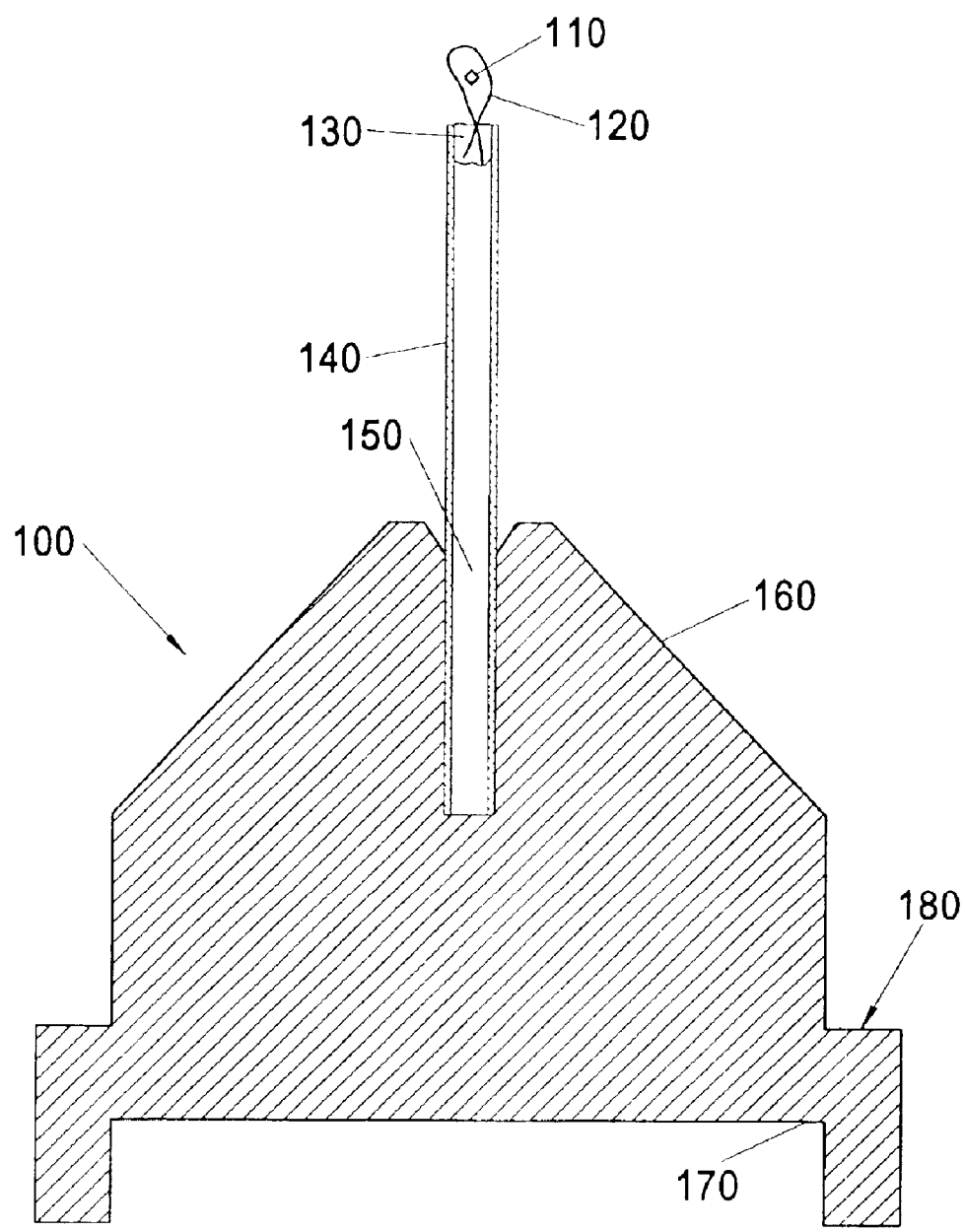
FIG. 1 is a cross sectional view of a sample assembly with a crystal sample mounted.

"Biological crystal" means a crystallized frozen biological material, preferably a cryogenically frozen biological material at near liquid nitrogen temperatures.

"Biological material" means either a collection of independent molecules, or a material having a non-covalently bound assembly of molecules derived from a living source. Examples include, but are not limited to, complexes of proteins, lipoprotein particles comprised of lipoproteins and lipids; viral particles assembled from coat proteins and glycoproteins; immune complexes assembled from antibodies and their cognate antigens, deoxyribonucleic acids (DNA), ribonucleic acids (RNA), polysaccharides, etc.

"Computer" means any device capable of performing the steps developed in this invention to result in an optimal waterflood injection, including but not limited to: a microprocessor, a digital state machine, a field programmable gate array (FGPA), a digital signal processor, a collocated integrated memory system with microprocessor and analog or digital output device, a distributed memory system with microprocessor and analog or digital output device connected with digital or analog signal protocols.

"Cryogenic" means a temperature at or below that of liquid nitrogen at standard atmospheric pressure, −195.79° C. or 77.36° K.

"Degree of freedom" means any one of the ways that a mechanical system can change spatial configuration, examples include, but are not limited to rotation, translation, and combinations of rotations and/or translations in one or more axes.

"Gage vacuum" means a relative pressure lower than ambient atmospheric pressure.

"Ferromagnetic" means a material capable of exhibiting alignment of atomic or molecular magnetic domains. Such a material is capable of magnetization, and is subjected to forces in the presence of a magnetic field.

"Goniometer" typically means a device for measuring angles. Herein, it is used somewhat differently in that it rotates a surface to particular angles as instructed by a computer device using internal reference angular measurements.

"Dewar" means any container for liquefied gases. These containers are traditionally typically double-walled with an evacuated interior having low thermal emissivity surfaces to reduce heat transfer from the container interior to the ambient atmosphere.

Overview

The present invention is directed toward the transportation and manipulation of samples of cryogenically frozen biological materials, preferably protein crystals mounted on sample assemblies comprised of a standardized base-pin configuration.

When the hardware components are computer operated as a fully integrated crystal mounting and alignment system for high-throughput biological crystallography (herein referred to as the "system"), remote sample mounting and alignment of individual samples to a predetermined position in space (for subsequent X-ray illumination) can be achieved in less than 30 seconds with minimal remote operator involvement. In some instances, samples have been remotely mounted and aligned in a cycle of 20 seconds. Since no human operator physical presence is required in the room where active x-ray irradiation is taking place, there is no prolonged sequence of doors or interlocks to safely admit an operator, further increasing the speed of sample cycling.

The sample assembly used in this invention is comprised of a sample base to which a thin sample tube is attached. The end of the sample tube not attached to the sample base has a sample loop, which contains the sample of frozen biological material to be examined. Typical samples range from 5–200 $\mu$m in size. The pin has a loop, which contains a cryogenically frozen sample.

The system for shipping, storing and handling the samples is comprised of a standardized sample cassette containing positions for a plurality of sample assemblies, preferably 16 sample assemblies each in the present design. The outer dimension (diameter) of these sample cassettes is constrained by the maximum inner diameter of a standard cryogenic transport container. Presently, a preferred standard cryogenic transport container will accommodate seven of these disks representing a maximum of 112 sample assemblies. Improvements on this design would allow even more sample assemblies in a higher packing density arrangement.

The computer-controlled high-throughput sample mounting and alignment system has been designed as a device optimized for reliable removal of the samples from the liquid nitrogen sample repository system and mounting on a sample positioner. The sample positioner, as further described below, positions the sample after it has been removed from the sample repository to a predetermined position in space through which an x-ray beam will subsequently pass, illuminating the sample and thereby generating crystallographic diffraction patterns. The major subsystems of the sample mounting and alignment system are: the sample positioner, a coordinated set of translational and rotating stages for positioning and orienting the sample gripper (known as the gripper stage), a repository system, a gripper defroster, an optical sample alignment system, and an x-ray camera. This system positions a sample crystal at a precise point in space for x-ray imaging analysis, or crystallography.

The sample repository system is principally a liquid nitrogen filled storage Dewar removably placed atop a position-addressable repository stage. It accommodates up to four sample cassettes on a cassette deck corresponding to 64 samples per load. The individual sample assemblies are held fixed in the storage Dewar by a machinable magnetic material that attracts and retains the ferromagnetic material in the sample assembly. The storage Dewar is mounted on a two axis movable platform that provides alignment of any one of the 64 samples on the cassette deck 700 (FIG. 7A) beneath the sample gripper (described below). By using a larger Dewar, more sample assemblies can be tested in one loading. Loads of 300 or more sample assemblies may be used.

In the preferred embodiment, the repository stage has one rotational degree of freedom, and one linear degree of freedom. By using a rotary stage atop a linear stage, valuable real estate is conserved, as the stage never has to move more than half of the diameter of the (preferably axisymmetric) storage Dewar.

The storage Dewar itself has external position referencing features that precisely and removably locate the storage Dewar atop the rotary and linear stages. The storage Dewar also has an internal referencing system that is aligned with the external position reference features. A removable cassette deck is placed through alignment pins in the internal referencing system. In this fashion, by placing the storage Dewar on the repository stage, individual sample assemblies mounted on the cassette deck can be moved to a specific location required for sample pickup and subsequent mounting. Samples can likewise be moved from one position to another (empty) position either on the same or different sample cassette.

The sample gripper contains a liquid nitrogen cooled split collet mechanism for grasping the sample assembly with sufficient force to overcome the magnetic attraction between the sample assembly base and the sample cassette base with its magnetic material, as well as to break free of any ice binding between them. The sample gripper is designed to encapsulate the sample tube with the sample crystal-containing sample loop within a liquid nitrogen temperature environment during the brief period when the gripper stage uses the sample gripper to transfer the sample assembly to the sample positioner.

The sample gripper contains a low thermal capacity (preferably very thin stainless steel) outer shroud, which provides a sheath-flow of warm dry gas to prevent icing and frost formation during exposure to ambient temperature, moisture-laden air. After the sample assembly is mounted, the sample is maintained in a cryostream of dry, near liquid nitrogen temperature gaseous nitrogen during subsequent crystallographic measurements. Sufficient cryostream flow is provided to maintain the sample at liquid nitrogen temperatures despite beam heating induced by the probing synchrotron-produced x-ray heat load and closely juxtaposed ambient atmosphere.

Removal of the sample assemblies from the sample positioner and replacement in the sample repository is accomplished using the same sample gripper. After removal, the mounting post upon which the sample assembly was just previously mounted could accumulate frost, interfering with the magnetic retention of the next sample assembly. If this frost becomes problematic, the mounting post could be actively heated.

The sample gripper is periodically warmed to remove any ice accumulation. The gripper defroster provides either heated dry nitrogen gas or heated dry air to the outer shroud of the gripper through a pattern of small holes. Due to the low thermal mass of the outer shroud of the sample gripper (recall that it is preferably very thin stainless steel), defrost typically occurs in 6 seconds or less. The upper part of the sample gripper is furthermore heated, allowing the sample gripper to be left in the liquid nitrogen Dewar indefinitely to keep it cold, but at the same time not damaging the pneumatic actuator mounted on top operating at near room temperature, which cannot be exposed to cryogenic temperatures.

The gripper stage moves the sample gripper through the mechanical motions used for removal and placement of the sample assembly between the sample positioning stage and the sample repository. The gripper stage comprises two orthogonal pneumatic translational motions (XY) (which could also be motor-controlled) upon which is mounted a third rotational ($\theta$) motion mechanism. A relatively low force pneumatic actuator, mounted on the rotational motion mechanism, provides further independent vertical movement. The low force pneumatic actuator prevents damage from the sample gripper impacting misplaced sample assemblies or frost.

The gripper stage motions are preferably based in part on pneumatic actuators to achieve precise and rapid motions in the liquid nitrogen cooled environment. The three-degree of freedom, (XY$\theta$) positioner of the gripper stage has been designed to move the sample gripper with the required positioning precision within the restricted allowable physical envelope of the experimental setup. Electrically powered motors and actuators could potentially replace some or all of these pneumatic actuators, however, pneumatic actuators have proven to be simpler, cheaper, and easier to control and maintain in this application.

The sample positioner is a three-degree of freedom stage, mounted on a precision goniometer to provide single axis rotation. The three-degree of freedom stage has been custom designed to position a sample assembly mounted on a mounting post at a precise position in the synchrotron x-ray beam, and, in coordination with the goniometer, to rotate the sample about that point. The three degree of freedom stage consists of two orthogonal motor-controlled translational motions (XY) upon which is mounted a third Z axis motion mechanism. By coordinating the motions of the XY stage and the goniometer, a mounted sample can be rotated about a defined point in space despite initial eccentric mounting. The overall hysteresis of the three degree of freedom stage is about 1.5 microns with a stability of about 1 micron. The system has been shown to be superior to existing commercial versions with respect to position precision and stability.

The optical alignment system that provides feedback for precise alignment of the sample is based upon a high-resolution zooming camera that is optically aligned to a point in space that will be subsequently illuminated by the synchrotron x-ray beam. A software reference pixel location for the center of the x-ray beam is initially established. Visual images of the mounted crystal sample are then compared with this reference. Any necessary positional corrections are calculated and executed by the sample positioner to position the sample over the software reference position.

The software and user interface designs have been structured to accommodate alternative centering feedback data based, for instance, on the measured x-ray intensities or data quality as indicated by the x-ray data collection imaging device.

It should be noted that the system described herein could be used for positioning cryogenically stored samples to a particular point in space for many alternative types of measurements. These measurements may be done by observing the sample at a single prescribed point in space, or by observing the sample at a variety of rotational angles as it is rotated by the goniometer. Depending on the relative time durations of the sampling measurement, the sample may be statically paused at each measurement, or may be continually rotated. An example of a continual rotation measurement could be that of short pulse-width laser illumination using short pulses having microsecond, nanosecond, or picosecond pulse-widths. With such short pulse-widths, even a moving sample appears as if it were stationary.

Data collection may be used on any experimental device outputting information that can be used as a measurement. Examples include, but are not limited to: x-ray crystallography, photonics-based tomography, photonics-based diffraction, surface spectroscopy, fluorescence correlation spectroscopy, photon arrival time interval distribution analysis, fluorescence resonance energy transfer methods, mass spectrometry, and evanescent wave methods, scanning probe microscopy, taccimetry, profilometry, and atomic force microscopy.

Sample Assembly

Referring now to FIG. 1, a sample assembly 100 is comprised of a sample 110 captured in a sample loop 120. The sample 110 is preferably frozen at cryogenic temperatures, such as that of liquid nitrogen at standard atmospheric pressure, −195.79° C. or 77.36° K. The sample loop 120 is in turn attached by adhesive 130, preferably alpha cyanoacrylate, to sample tube 140. The sample tube 140 is attached to sample base 160 by insertion into hole 150. The sample base 160 has an upper land 180 for retention, and a lower recess 170 for mounting.

Sample base 160 is ferromagnetic, preferably easily free-machining ANSI 1118 steel with zinc electroplating after machining for corrosion resistance. The sample tube 140 is preferably stainless steel or other low thermal conductivity material, preferably already containing an attached 50 to 1000 $\mu$m nylon sample loop 120.

Sample Cassette

Referring now to FIGS. 2A, 2B and 2C, a sample cassette 200 holding one sample assembly 100 is shown. The sample cassette 200 has a cassette base 210 into which a keyed shaft 220 is affixed on one end 225. A magnet 250, preferably a machinable magnet of polymeric matrix material, is inserted into the cassette base 210, preferably in a recess 255 in the cassette base 210. The machinable magnet 250 has one opening 230 aligned with each corresponding cassette base opening 265. Sample assemblies 100 are then able to be loosely inserted into cassette base 210 through openings 265 and be retained by the upper surface 260 of magnet 250, with cooling liquid nitrogen able to flow through each magnet 250 opening 230 and cassette base 210 opening 265 to directly contact, and hence, cool the sample assembly 100 through direct contact with lower recess 170 (shown in FIG. 1).

In this embodiment of the sample cassette 200, 16 sample assemblies can be accommodated in a regular pattern forming two concentric circles. However, any other regularized or nonregularized pattern (not shown in FIG. 2B) could be used as well.

Keyed shaft 220 is present to align a cassette cover 300 (described below) so that it does not damage the samples 110 when they are covered for transport or storage. Many other functionally equivalent methods, using multiple unkeyed shafts in a pattern, or external jigs, would also achieve the result that cassette cover 300 placement onto the sample cassette 200 would not damage any of the samples 110. The attachment of keyed shaft 220 is preferably by a threaded screw into a threaded recess in the keyed shaft, however, many other mechanically equivalent attachment methods would also work, including, but not limited to press fit, shrink fit, adhesive attachment, welding, or threading.

Sample Cassette Cover

Figure 3A:
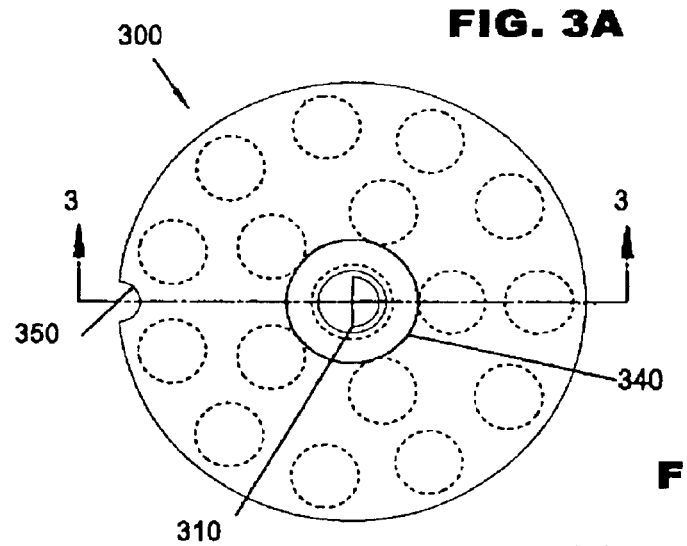
FIG. 3A is a top view of a sample cassette cover.
Figure 3B:
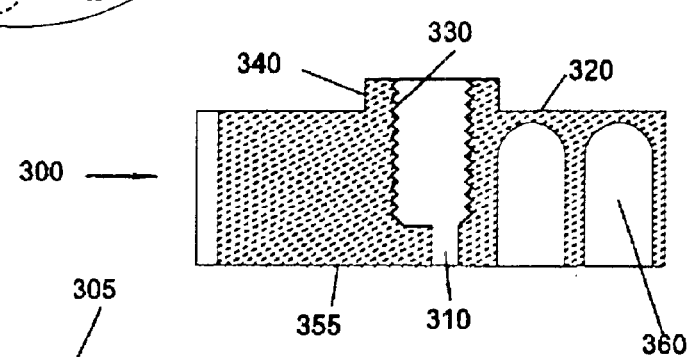
FIG. 3B is a cross sectional view through section 3—3 of FIG. 3A of a sample cassette cover.
Figure 3C:
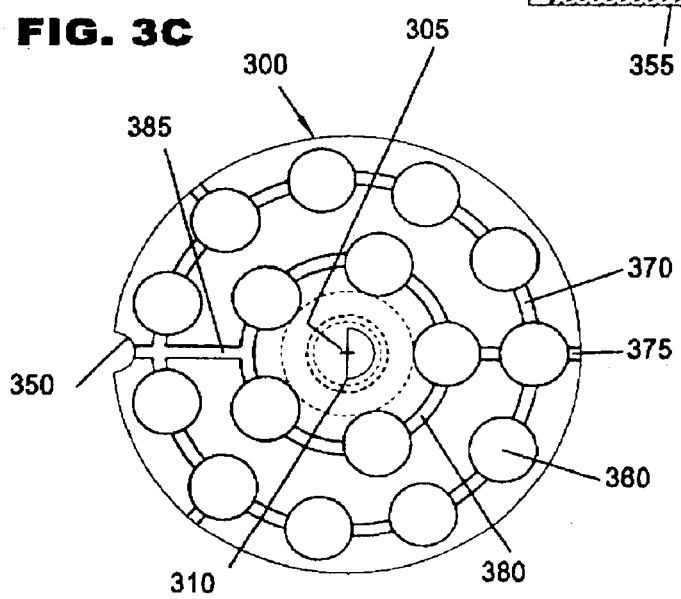
FIG. 3C is a bottom view of a sample cassette cover showing liquid nitrogen venting features.

Referring now to FIGS. 3A, 3B and 3C, a sample cassette cover 300 is a cylindrical shape with a keyed opening 310 passing through a threaded section 330. A cylindrical neck 340 portion protrudes above the main top surface 320, and is centered on the sample cassette cover 300 center 305. An indexing feature 350 serves as clearance for an alignment feature to be discussed below.

In the sample cassette cover 300 bottom surface 355, pluralities of sample assembly recesses 360 provide protection to samples assemblies 100 (shown in FIG. 1) placed in them. In this embodiment, an outer vent ring 370 and an inner vent ring 380 vent the sample assembly recesses 360; these details are not shown with hidden lines in FIG. 3A to minimize confusion of hidden lines. The outer vent ring 370 and an inner vent ring 380 are respectively ported to the exterior of the sample cassette cover 300 with pluralities of outer vent ports 375 and inner vent ports 385. This venting arrangement allows for the flow of liquid nitrogen to each of the sample assembly recesses 360, ensuring that sample assemblies 100 (shown in FIG. 1) as well as the cassette cover 300 are amply cooled by liquid nitrogen. It also allows the venting of nitrogen gas, which might otherwise build up inside the sample assembly recesses 360.

Sample Cassette Assembly

Figure 4A:
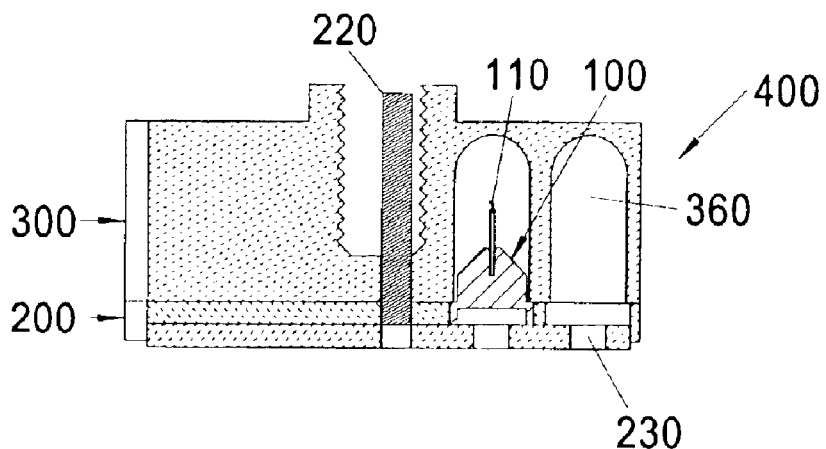
FIG. 4A is a cross sectional view of a sample cassette assembly comprised of an assembled sample cassette with one sample assembly, and protected by a sample cassette cover.
Figure 4B:
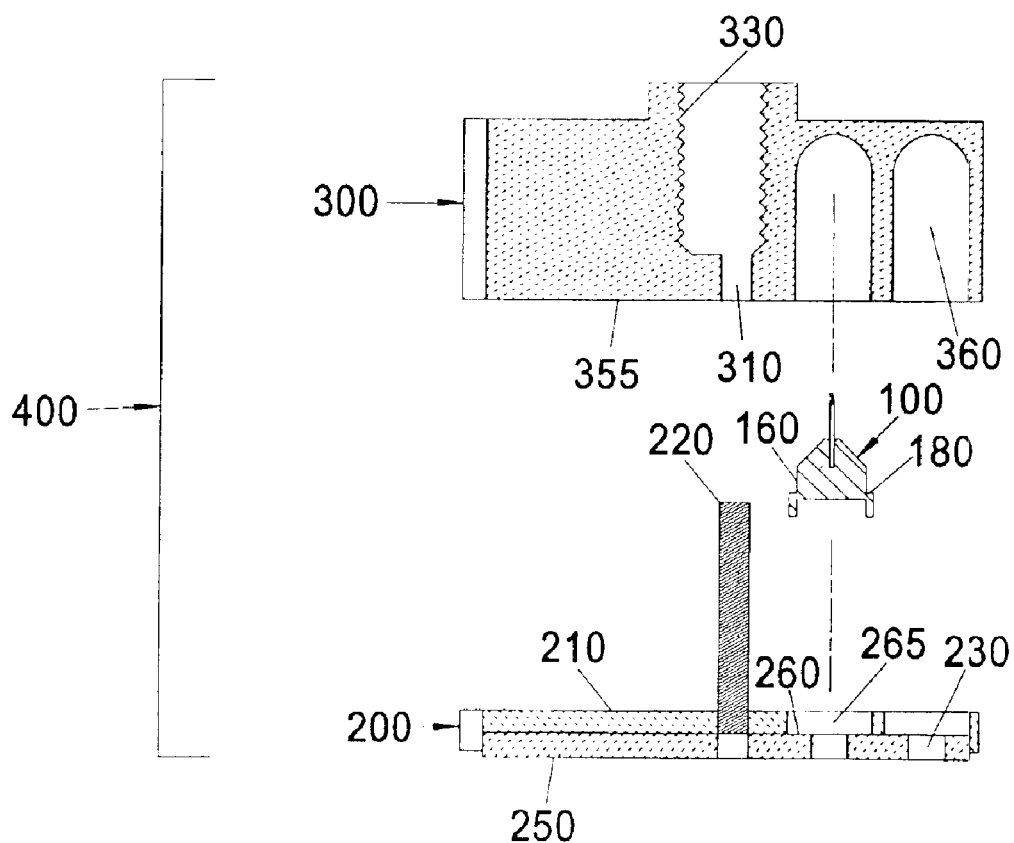
FIG. 4B is an exploded cross sectional view of a sample cassette assembly comprised of a sample cassette, one sample assembly, and a sample cassette cover, before assembly.

Referring now to FIG. 4A, a sample cassette assembly 400 is shown comprised of a sample cassette cover 300 assembled in place over a sample assembly 100, and retained by sample cassette 200. Now referring to both FIGS. 4A and 4B, sample assembly 100 is magnetically retained on the upper surface 260 of magnet 250.

During installation, the sample cassette cover 300 first encounters keyed shaft 220. The sample cassette cover 300 must first be rotationally aligned relative to sample cassette 200 so that the keyed shaft 220 may translate into the keyed opening 310. Since the keyed shaft 220 is taller than the installed sample assembly 100, the sample 110 cannot be damaged by the sample cassette cover 300 during normal installation of the sample cassette cover 300 as sample assembly recesses 360 in the sample cassette cover 300 slides over each of the sample assemblies 100.

The sample cassette cover 300 has one sample assembly recess 360 for each matching cassette base 210 opening 265. The depth of the sample assembly recesses 360 exceeds the retained height of the sample assembly 100. Additionally, the sample assembly recesses 360 have smaller diameters than the width of the sample assembly 100, so that the bottom surface 355 of the sample cassette cover 300 positively retains the sample base 160 by contacting upper land 180.

When assembled as shown in FIG. 4A, the sample assemblies 100 are positively sandwiched between the sample cassette cover 300 and the sample cassette 200. Now referring additionally to FIG. 3C, the outer vent ring 370 and the inner vent ring 380 allow for filling of the sample assembly recesses 360 with liquid nitrogen through outer vent ports 375 and inner vent ports 385.

In one embodiment of the invention, the assembled cassette cover 300 and sample cassette 200 are inverted so that sample assembly recesses 360 form liquid nitrogen repositories, thus keeping the biological crystal sample 110 immersed in liquid nitrogen and maintaining the sample at a cryogenic temperature until all of the liquid nitrogen has boiled away. In this embodiment, several minutes of room temperature exposure can be tolerated by the sample with minimal temperature rise when moving samples from shipping container to cryogenic sample repository.

Additional mechanical components (not shown) clip and retain the sample cassette cover 300 to the sample cassette 200, although many other methods of positively retaining the parts together exist, and are readily designed by those skilled in the mechanical design arts.

Sample Cassette Carrier

Refer now to FIGS. 5A and 5B, where a cassette carrier 500 is depicted. A top hook 510 is press fit into a low thermal conductivity sleeve 515, preferably comprised of fiberglass or other low thermal conductivity low temperature plastic, which has inserted into it a stainless steel rod 520. The stainless steel rod 520 is welded to a tab 525 formed by two narrow slots 530 on either side. The tab 525 is part of a sheet 580 that encompasses, and is attached to, about half the diameter of a plurality of shelves 550. The method of attachment could be any that survives repeated thermal shocks from room temperature to liquid nitrogen temperature. In this embodiment, three screws 590 are used to attach each shelf 550 to the sheet 580.

The distances between the shelves 550 form a set of shelf openings, or landings 535. For purposes of illustration, the top-most landing 535 is vacant, without a sample cassette assembly 400. The other six shelve openings in the diagram each show sample cassette assemblies 400 present.

In FIG. 5B, each shelf 550 has an inner 551 and outer 552 radius concentric about a center point 555, which is the same center point for a mounted sample cassette assembly 400. During insertion of the sample cassette assembly 400, cylindrical neck 340 (shown in FIGS. 3A and 3B) of the sample cassette cover 300 slides into obround slot 560, where retaining spring 570, secured by fastener 575, retains the sample cassette cover 300. Retaining spring 570 deflects partially into retaining spring recess 565. When fully inserted, cassette cover 300 center 305 is roughly concentric with center point 555.

Cryogenic Transport Container

Figure 6:
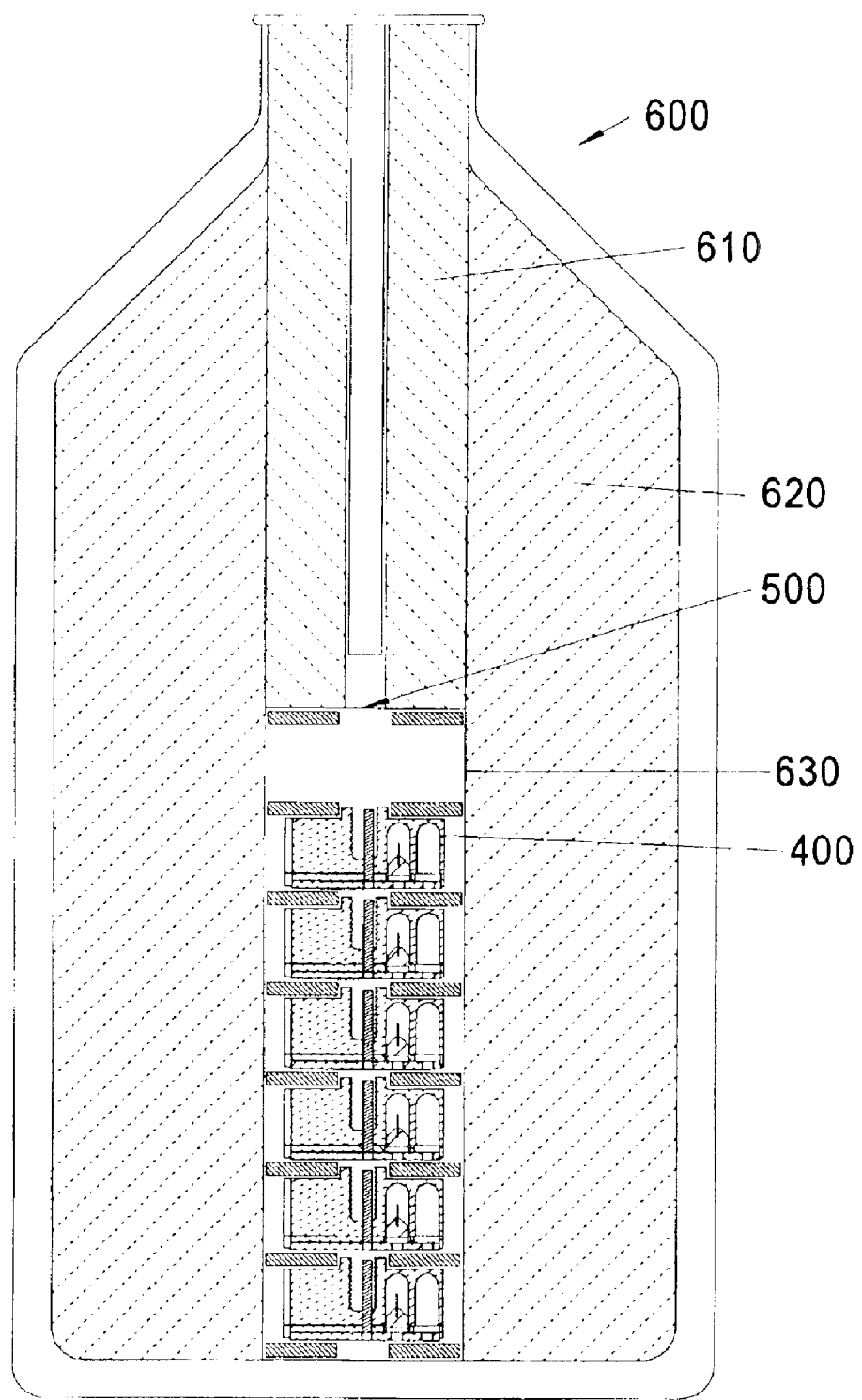
FIG. 6 is a cross sectional view of a cryogenic shipping container with sample cassette carrier with six sample cassette assemblies present, and the top slot vacant.

Before shipping, the cryogenic transport container 600 of FIG. 6 is initially precooled with liquid nitrogen for shipping per the manufacturer's directions. Some of these precooling steps can take as long as four hours to complete.

Referring now to FIG. 6, cryogenic transportation container 600 has a removable insulation plug 610, which inserts into a corresponding cylindrical bore 630 in bulk insulation 620. When cylindrical bore 630 is initially empty except for nitrogen gas and liquid, the cassette carrier 500, having one or more sample cassette assemblies 400, is first inserted. Subsequently, the removable insulation plug 610 is installed. Further liquid nitrogen, if needed, is added per the manufacturer's directions. Depending on the manufacturer of cryogenic transportation container 600, ambient temperature exposure, and the detailed construction of the container, cryogenic temperatures below −150° C. can be maintained during shipment for up to 200 hours.

Cassette Deck

Figure 7A:
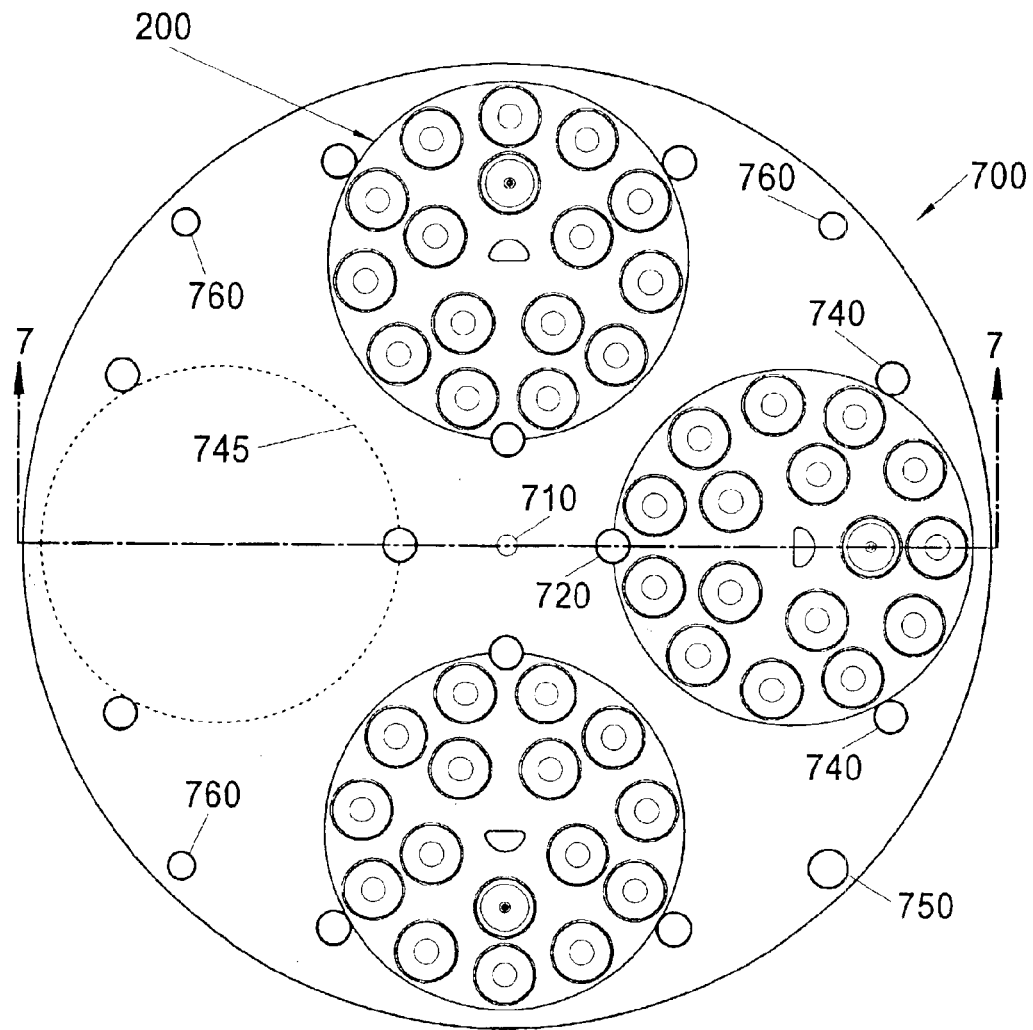
FIG. 7A is a top view of a cassette deck with three sample cassettes present and one sample cassette absent.
Figure 7B:
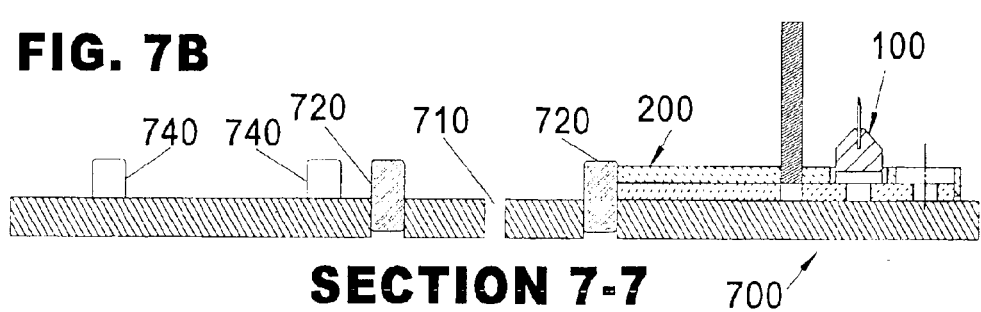
FIG. 7B is a sectional view of the cassette deck of FIG. 7A with three sample cassettes present and one sample cassette absent.

Refer now to FIGS. 7A and 7B. The cassette deck 700 is shown. The cassette deck 700 has a center reference hole 710, three mounting holes 760, and a larger diameter keying hole 750 to uniquely orient the cassette deck 700 with respect to hardware incorporated into the sample repository (not shown). Orientation pins 720 are preferably press fit into the cassette deck 700. The orientation pins 720 provide a unique orientation of sample cassettes 200 which are positioned between the two other outer positioning pins 740. This pattern is replicated in four quadrants. In one quadrant there is just an outline of the area 745 that is normally occupied by a sample cassette 200.

By using this arrangement, in conjunction with the sample cassette 200 design, all sample assemblies 100 are uniquely positioned with respect to the cassette deck 700. The unique positioning allows for unattended sample assembly 100 mounting and demounting using a sample gripper described below.

Sample Gripper

Figure 8:
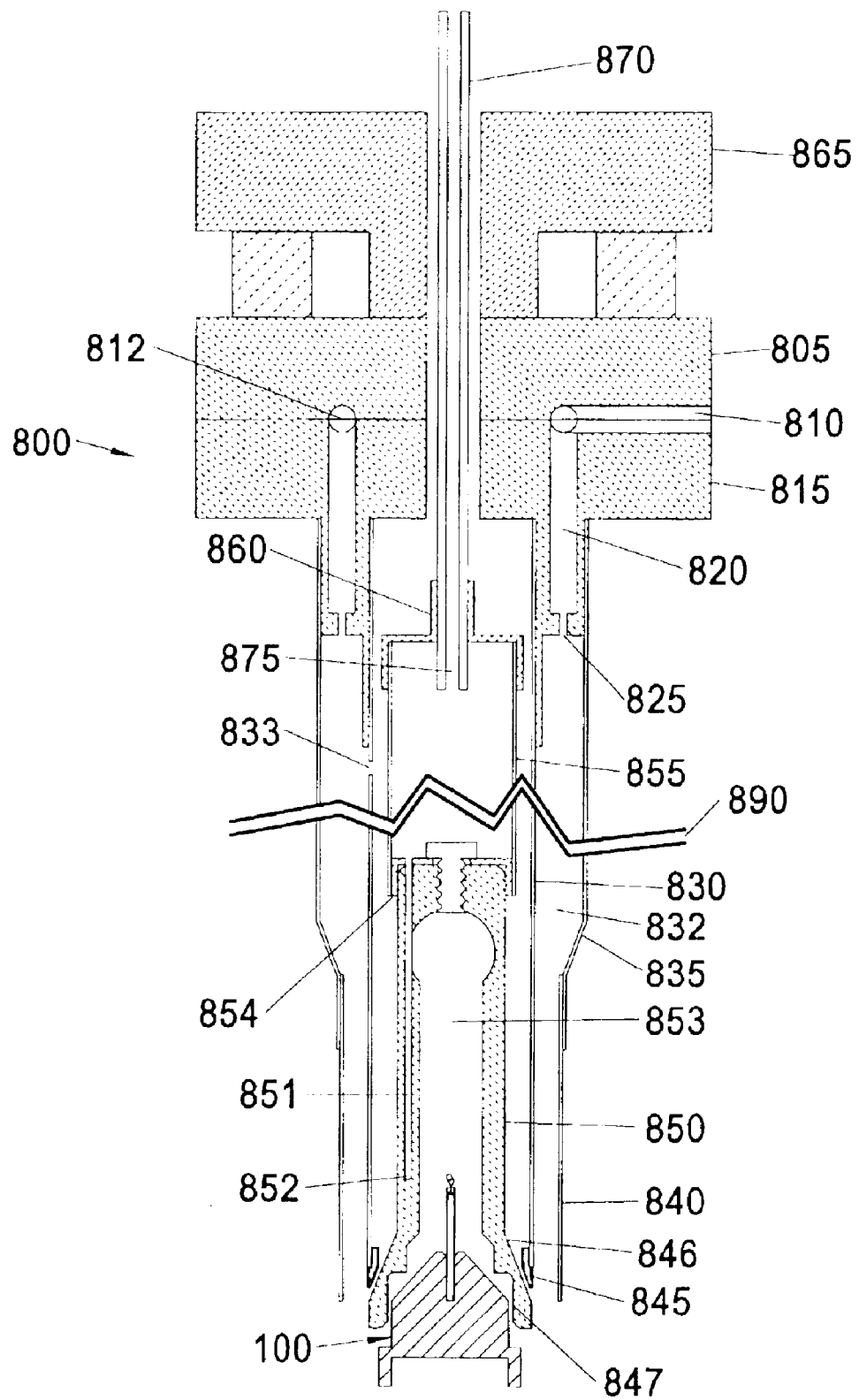
FIG. 8 is a cross sectional view of a sample gripper.

The sample gripper 800 is shown in FIG. 8. An upper actuator flange 865 is connected to a lower actuator flange 805. The actual mechanism of the actuator is not shown, as these are readily commercially available as either solenoidal electrical or pneumatic force/displacement devices. The preferred actuator is pneumatic. The lower actuator flange 805 has been modified so that in conjunction with gripper flange 815, a port 810 is formed. The port 810 attaches to a plenum 812. The plenum 812 allows a continuous gas connection with a series of cylindrical openings 820, which at their apex, connect to small openings 825. Input gas can be attached to port 810, fill plenum 812, pass through a plurality of cylindrical opening 820, and emit at small openings 825 into an outer shroud area 832. The outer shroud area 832 is formed by an inner tube 830 and outer tube 835, which are both attached to gripper flange 815. The outer tube 835 necks down to a removable close fitting shroud tube 840. The inner tube 830 has a very low thermal mass, low heat capacity material, and is preferably both very thin walled, and made of stainless steel. At the lower end of the inner tube 830, is attached a collet sleeve 845. The collet sleeve 845 is preferably silver soldered (not shown) to the stainless steel inner tube 830. The inner tube 830 must be sufficiently thick so as to keep from bucking under axial compressive forces generated by the collet sleeve 845.

The split collet 850 has an actuation movement relative to the collet sleeve 845, closing the split collet 850 about a sample assembly 100 located within its grasp. When split collet 850 is retracted upwards, the collet sleeve 845 causes compressive closure of the collet actuation surface 846, with consequent high force retention of the sample assembly 100 located within the split collet 850 in a collet recess 847. The split collet 850 is pulled upward by collet adapter 854, which connects the split collet 850 to the collet tube 855. The collet tube 855 is in turn connected to the actuator adapter 860. The actuator adapter 860 connects collet tube 855 to the actuator tube 870. Thus a vertical motion of the actuator tube 870 causes the same vertical motion of the actuator adaptor 860, collet tube 855, collet adapter 854, and in turn the split collet 850.

The temperature of the split collet 850 is measured by a temperature sensing element 852 located at the bottom of a temperature sensing hole 851. Wires (not shown to minimize drawing clutter) ascend upward through the temperature sensing hole 851, through a matching hole in collet adapter 854, and exit the sample gripper 800 through the center bore 875 of actuator tube 870.

To cool the sample gripper 800 down to temperatures appropriate for sample assembly 100 pickup (e.g. liquid nitrogen temperature), the collet sleeve 845 end of the sample gripper 800 is immersed in liquid nitrogen. At this time, there is no sample assembly 100 present. A small gage vacuum of 3–4 inches of mercury is drawn on port 810, which is communicated through the small openings 825 to the outer shroud area 832. Vent port 833 in inner tube 830 allows the vacuum to pull liquid nitrogen up and around split collet 850. Since the collet is split, liquid nitrogen fills the interior 853 of the split collet 850. The temperature-sensing element 852 is used to register when the split collet 850 temperature has cooled sufficiently for sample assembly 100 pickup.

When the sample gripper 800 is moving the sample assembly 100, room temperature dry nitrogen gas is fed through port 810 into the outer shroud area 832 to preclude frost buildup on inner tube 830 or split collet 850. The frost buildup is prevented by the simple expedient of keeping moisture away from any of the cold surfaces of the inner tube 830 or split collet 850, by the flow of the dry nitrogen gas, preferably in laminar flow.

The sample gripper 800 is drawn showing most details, with the center section abbreviated by a cut 890.

Figure 9A:
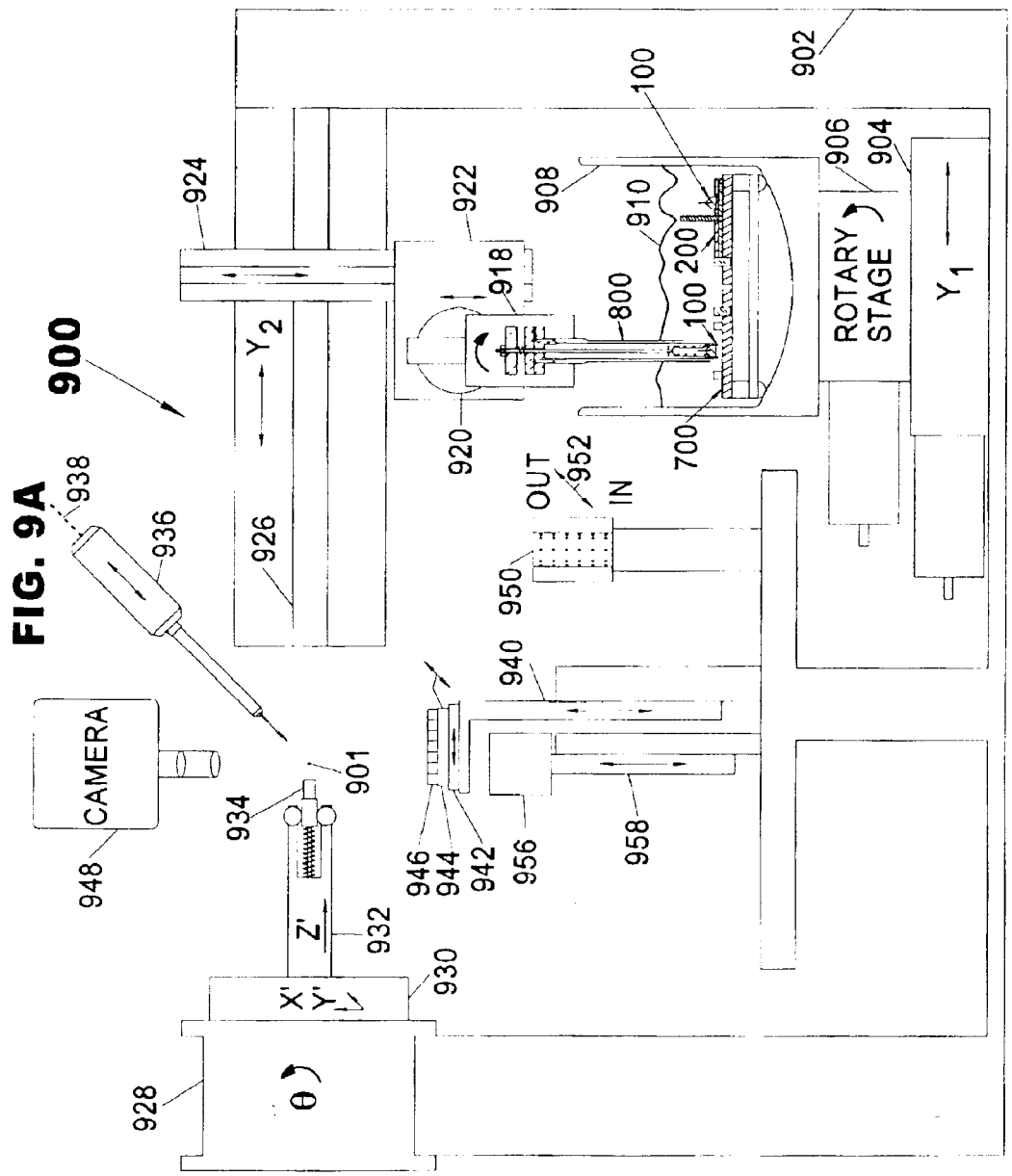
FIG. 9A is a partial front view of the integrated robotic crystal mounting and alignment system showing most of the major subsystems, where the system has just grasped a sample assembly in the sample repository.

Integrated Crystal Mounting and Alignment System for High-throughput Biological Crystallography Referring now to FIG. 9A, we see the integrated crystal mounting and alignment system for high-throughput biological crystallography 900 as viewed down an axis parallel to the incoming synchrotron x-ray beam 901. A frame 902 connects the various subsystems, and will not be fully described other than to say that it must be sufficiently stable and stiff to keep most components accurately positioned to within about 1 μm.

The subsystems include a repository stage, a gripper stage, a sample positioner, a cryostream unit, a video alignment subsystem, and a collimation and beam blocking subsystem. These subsystems are more fully described sequentially below.

The repository stage is comprised of the $Y_1$, linear stage 904, which is mounted on the frame 902. Atop the $Y_1$, linear stage 904 is attached rotary stage 906, which rotates about a vertical axis of revolution. Storage Dewar 908 removably attaches to the rotary stage 906 at a repeatable position and orientation using standard mechanical and precision engineering fixturing techniques that are well known in these arts. The storage Dewar 908 is nominally filled with enough liquid nitrogen 910 to amply cover any sample assemblies 100 that may be present in any sample cassettes 200. The cassette deck 700 is mounted on position referencing components not described here, which allows sample cassettes 200 to be addressably positioned relative to the frame 902 with high accuracy.

Figure 9D:
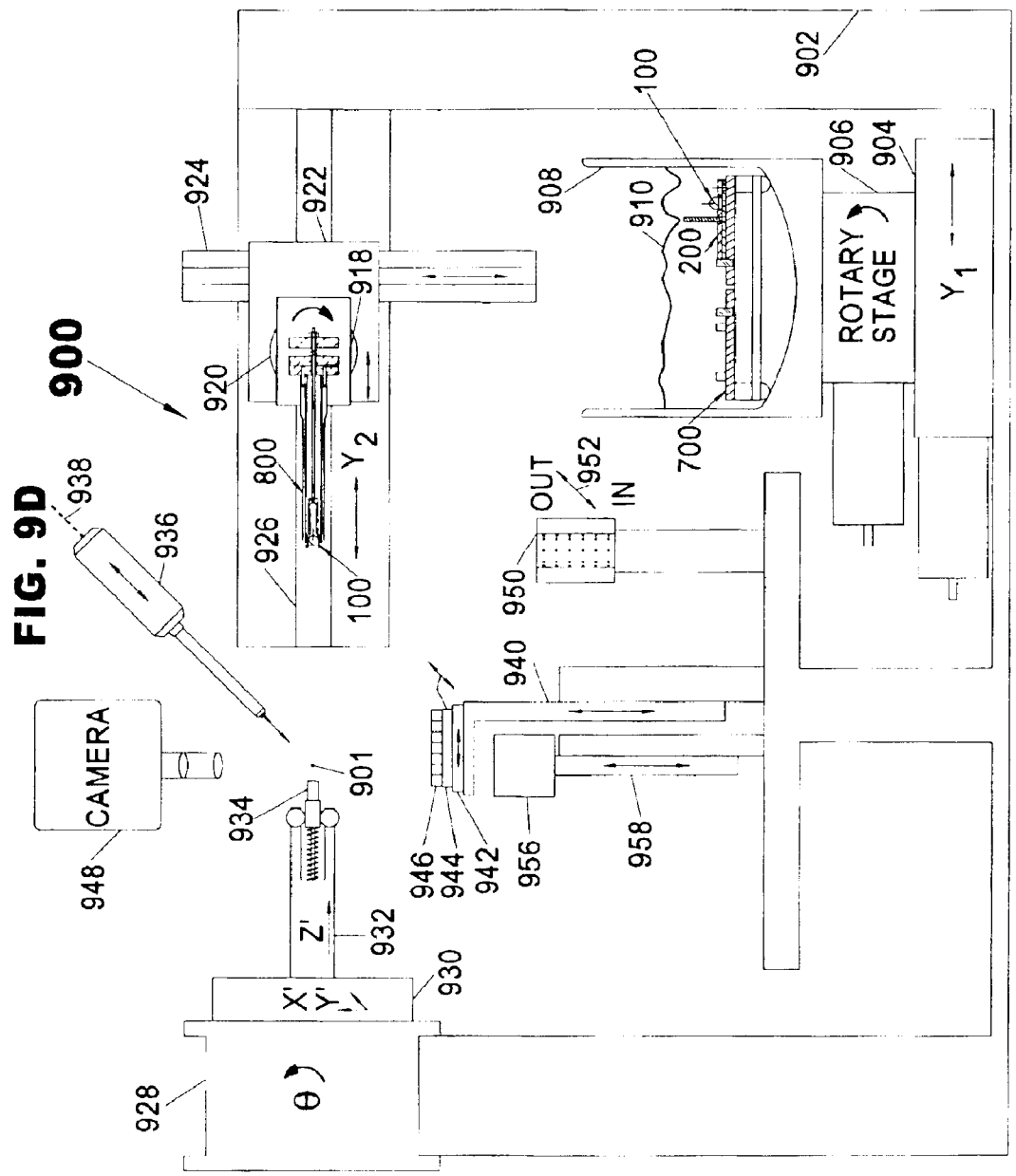
FIG. 9D is a partial front view of the integrated robotic crystal mounting and alignment system showing most of the major subsystems, where the system has rotated the pneumatic 90° rotary stage, known as Rotary, causing the sample gripper to rotate toward the sample positioner.

The gripper stage moves the sample gripper 800 relative to the frame 902. It comprises a horizontal stage 926, an UpDown stage 924, and a rotary stage 920. A long travel $Y_2$ linear stage, known as the horizontal stage 926, moves horizontally (along the plane of the paper) a vertical stage mounted transversely thereon, known as UpDown 924. The UpDown stage 924 comprises a platform 922 that serves as a mounting base for a 90° rotary stage 920, known as Rotary, preferably a pneumatic 90° rotary stage. The 90° rotary stage 920 top mounts a small travel, lighter actuation force pneumatic stage called SmallMove 918, which serves as a mount for the sample gripper 800. Rotary stage 920 rotate the sample gripper 800 between a downward position (as shown in FIG. 9C) and a horizontal position (as shown in FIG. 9D).

The sample positioner is comprised of a high precision rotary stage known as a goniometer 928, which is mounted on the frame 902. The goniometer 928 rotates an angle θ (theta) along an axis typically parallel to the horizontal plane. Upon the goniometer 928 is mounted a. A Z' stage 932 with a magnetic mounting post 934 mounts onto the X'Y' stage 930. At the particular goniometer 928 angle θ depicted in FIGS. 9A–9G, the X'Y' stage 930 moves in and out of the plane of the paper (the X' axis), and up and down in the plane of the paper (the Y' axis). These motions will rotate with continued rotations of the goniometer 928 in a typical kinematic rotating frame of reference. The mounting post 934 is mounted upon, and moved by, compound X'Y' stage 930. The mounting post 934 is spring preloaded (to prevent hard sample assembly 100 mountings), and rides on two sets of three bearings, each set of which forms an equilateral triangle.

Figure 10A:
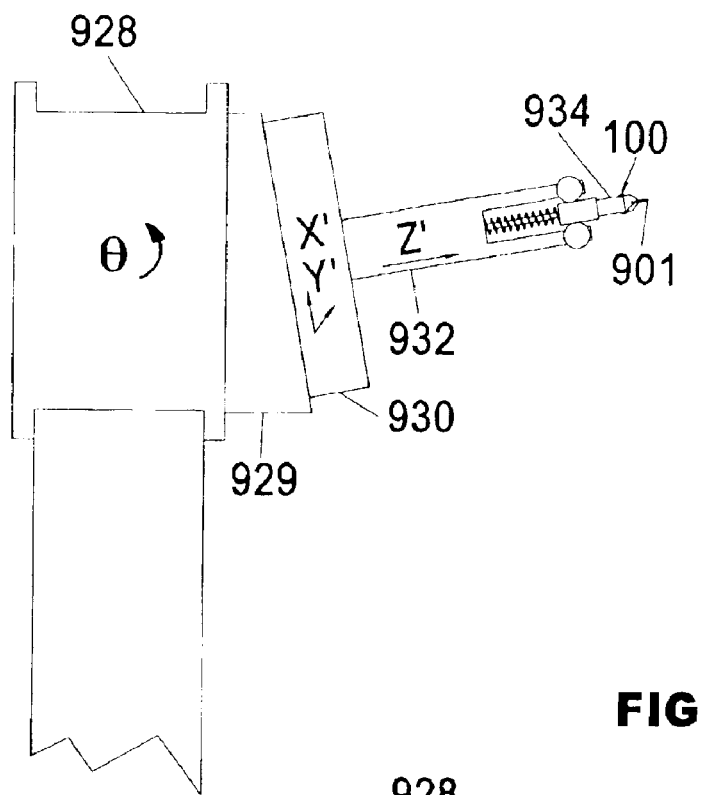
FIG. 10A is a partial front view of the sample positioner, including a tilt plate disposed between a goniometer and the X' Y' compound stage.

In an alternate embodiment of the system, the sample positioner is further comprised of a tilt plate 929 (as depicted in FIG. 10A) disposed between the high precision rotary stage known as the goniometer 928, and the compound X'Y' stage 930, to which the Z' stage 932 is attached as before. The effect of the tilt plate 929 is to rotate the Z' stage 932 eccentrically with respect to the axis of rotation of the goniometer 928 so that the positioner rotates the sample 110 about an axis non-orthogonal with the compound X'Y' stage 930 and the Z' stage 932. The tilt plate 929 preferably forms a tilt angle of at least 15°, more preferably of at least 10°, yet more preferably of at least 5°, still more preferably of at least 2°, and most preferably of at least 1°. The alignment and centering operations described below may be used either directly by ignoring the effect of the tilt plate 929, or by including the angle of the tilt plate 929 in the alignment and centering algorithms. Regardless of the eccentricity induced by the tilt plate 929, the properly centered sample 110 will maintain location within the x-ray synchrotron beam 901 when the beam is operational, and the same spatial position when the x-ray synchrotron beam 901 is non-operational, as further described below. Rotations of the sample 110 will normally require operation of the compound X'Y' stage 930 and the Z' stage 932 for correct positioning.

Figure 10B:
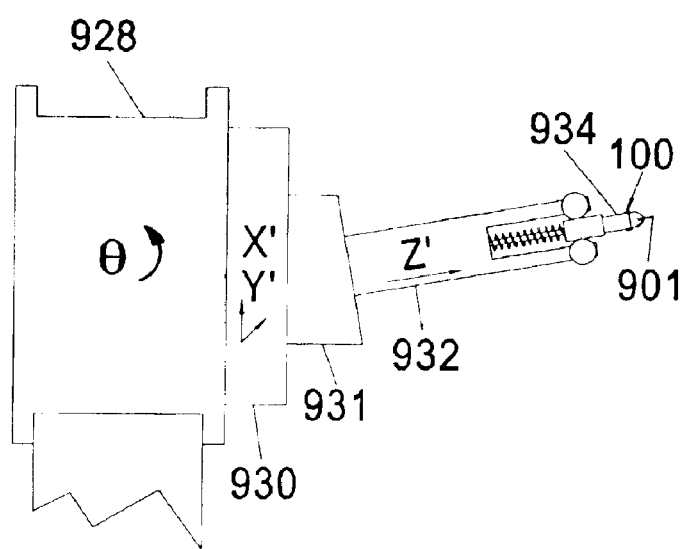
FIG. 10B is a partial front view of the sample positioner, including another tilt plate disposed between the X' Y' compound stage and the Z' stage.

In yet another embodiment (shown in FIG. 10B) another tilt plate 931 may be disposed between the compound X'Y' stage 930 and the Z' stage 932 to effect the eccentricity described above. In this further embodiment, the other tilt plate 931 would preferably form a tilt angle of at least 15°, more preferably of at least 10°, yet more preferably of at least 5°, still more preferably of at least 2°, and most preferably of at least 1°.

In operation, a sample assembly 100 (already removed here, and thus not shown) is retained by the mounting post 934 by magnetic attraction. The mounting post 934 could readily be heated to prevent frost formation, but heating has not yet proven necessary. The coordinated motions of the rotation addressable goniometer 928, the compound X'Y' stage 930 and the Z' stage 932 allow a sample to be rotated in space about a predetermined point, preferably the incoming synchrotron x-ray beam 901.

A commercially available cryostream unit 936 emits a stream of near liquid nitrogen temperature nitrogen gas to cool the sample 110 when the sample assembly 100 is mounted on the mounting post 934. The cryostream unit 936 is actuated along axis 938 so as to: 1) prevent interference with the sample gripper 800 when mounting or unmounting sample assemblies 100 (not shown), 2) not optically occlude the camera 948 optical aperture, and 3) not interfere with the projection of the incoming synchrotron x-ray beam 901, regardless of whether or not the x-ray beam 901 is operational.

The video alignment subsystem is comprised of a commercially available backlighter 956 on a vertically extendible backlighter stage 958. During alignment, the backlighter stage 958 raises the backlighter 956 so that the sample 100 (not shown, but mounted on mounting post 934) is back-lit when viewed by the high resolution macroscopic zooming video camera 948. During x-ray irradiation, the backlighter 956 is retracted so that it is out of the direct x-ray beam 901.

Collimation and beam blocking is typically required to respectively form a parallel incoming x-ray beam of a controlled diameter, or stop the beam altogether. For collimation to work properly, a small aperture must be aligned with the incoming x-ray beam. Collimation and beam blocking of the x-ray beam is effected by using the collimator vertical actuator 940 to raise a piezoelectric actuator 942, to which an x piezoelectric actuator 944 is attached, which moves a selection of collimators having various diameters and beam blocks 946 into the x-ray beam 901. Note that the collimators and beam blocks 946 with their associated actuators, are in a non-interfering plane from the backlighter 956 so that each may operate independently without collision.

To collimate or locally block the synchrotron x-ray beam 901, the various diameter collimators and beam block 946 is moved up into the x-ray beam 901 by the collimator vertical actuator 940, and is precisely positioned for optimal collimation by small, precise movements effected by piezoelectric actuators 942 and 944.

Application of the Invention to Mount a Sample Assembly

Refer now to FIGS. 9A–9F, which is a sequence of partial front views of the integrated crystal mounting and alignment system for high-throughput biological crystallography 900 with most of the major subsystems illustrated. The sequence of FIGS. 9A–9F show some of the major steps involved in conveying a sample assembly 100 to the sample positioner mounting post 934 for alignment using camera 948 and subsequent data collection from crystallographic diffraction of the incoming synchrotron x-ray beam 901 by the sample 110 (not shown).

Initially, the sample gripper 800 must be cooled sufficiently to safely grasp a sample assembly 100. The sample gripper 800 is initially partially immersed in the liquid nitrogen 910 so that the temperature-sensing element 852 (shown in FIG. 8) is cooled to a temperature of at least –150° C. prior to continuing with the sample assembly pickup. This initial sample gripper 800 immersion is located away from any resident sample assemblies 100 present in the storage Dewar 908. For this purpose the sample gripper 800 is immersed in the storage Dewar 908 until a set temperature is achieved. This initial cooling procedure typically requires over a minute. However, in normal operation, the cooling down procedure is only required once in a set of samples since the sample gripper 800 remains cold with repeated immersions in the liquid nitrogen 910. When a sample assembly 100 pickup occurs, further additional cooling will take place as the sample gripper 800 is immersed in the storage Dewar 908.

FIGS. 9A–G correspond to the integrated crystal mounting and alignment system 900 moving through a sequence of configurations as described more fully below. It is appreciated that there are many alternative sequences and minor variations that may be used to effect the same operations.

In FIG. 9A, the system is in the process of using the sample gripper 800 to grasp a sample assembly 100 in the storage Dewar 908. From there, it will move the sample assembly 100 to the sample positioner mounting post 934 for alignment and x-ray probing. At this step in the protocol, a sample assembly 100 has been grasped by sample gripper 800. Prior to grasping the sample assembly 100, the following setup steps have occurred: (1) the gripper 800 is released; (2) the heater 950, collimator beam blocks 946, the cryostream unit 936 are retracted so as to not interfere with other movements; (3) Rotary 920 is rotated down so that the sample gripper 800 assumes a vertical orientation; (4) UpDown 924 has been moved down; (5) SmallMove 918 has been downwardly extended; and (6) the gripper stage has moved the sample gripper 800 to a location in the storage Dewar 908, and immersed the sample gripper 800 in the liquid nitrogen 910 until the sample gripper 800 has reached a temperature of –130° C. as measured by the temperature sensing element 852 (indicated but not shown in FIG. 8). Gripping is accomplished by moving the sample gripper 800 over a selected sample assembly 100 located in a predefined location pattern in the storage Dewar 908. The sample gripper 800 is actuated, causing the split collet 850 to exert a pressure on the sample assembly 100. The friction generated by this pressure is sufficient to overcome the frost buildup and/or magnetic attraction of the sample assembly 100 to the sample cassettes 200 in the storage Dewar 908.

Next, in FIG. 9B, the system has retracted the SmallMove 918 pneumatic stage, causing the sample gripper 800 to be moved vertically upwards. Depending on the liquid nitrogen 910 fill level in the storage Dewar 908, the sample assembly 100 may have cleared the liquid nitrogen 910 surface, as depicted here. Not shown in the drawings is an automated liquid nitrogen fill apparatus, to keep the liquid nitrogen 910 fill level at a specified level. The storage Dewar 908 is typically nearly full, so that the sample gripper 800 is partially immersed even when SmallMove 918 is retracted to its highest vertical position.

Next, in FIG. 9C, the system has actuated the transverse vertical stage, known as UpDown 924, causing the platform 922 to move further vertically upwards, carrying the sample gripper 800 vertically upwards, so that the grasped sample, assembly 100 vertically clears the top of the storage Dewar 908.

Next, in FIG. 9D, the system has rotated the pneumatic 90° rotary stage 920, known as Rotary, causing the sample gripper 800 and sample assembly 100 to rotate 90° clockwise and point toward the sample positioner mounting post 934. Sample assembly 100 is essentially collinear with mounting post 934.

Next, in FIG. 9E, the sample gripper 800 has moved by the long horizontal travel linear stage, known as the $Y_2$ stage 926, causing the sample gripper 800 to move to a predetermined distance toward the sample positioner mounting post 934, in a vector parallel to the Z' stage 932 motion (horizontally as indicated in FIG. 9E), with sample assembly 100 approaching the mounting post 934 in advance of sample gripper 800.

Figure 9F:
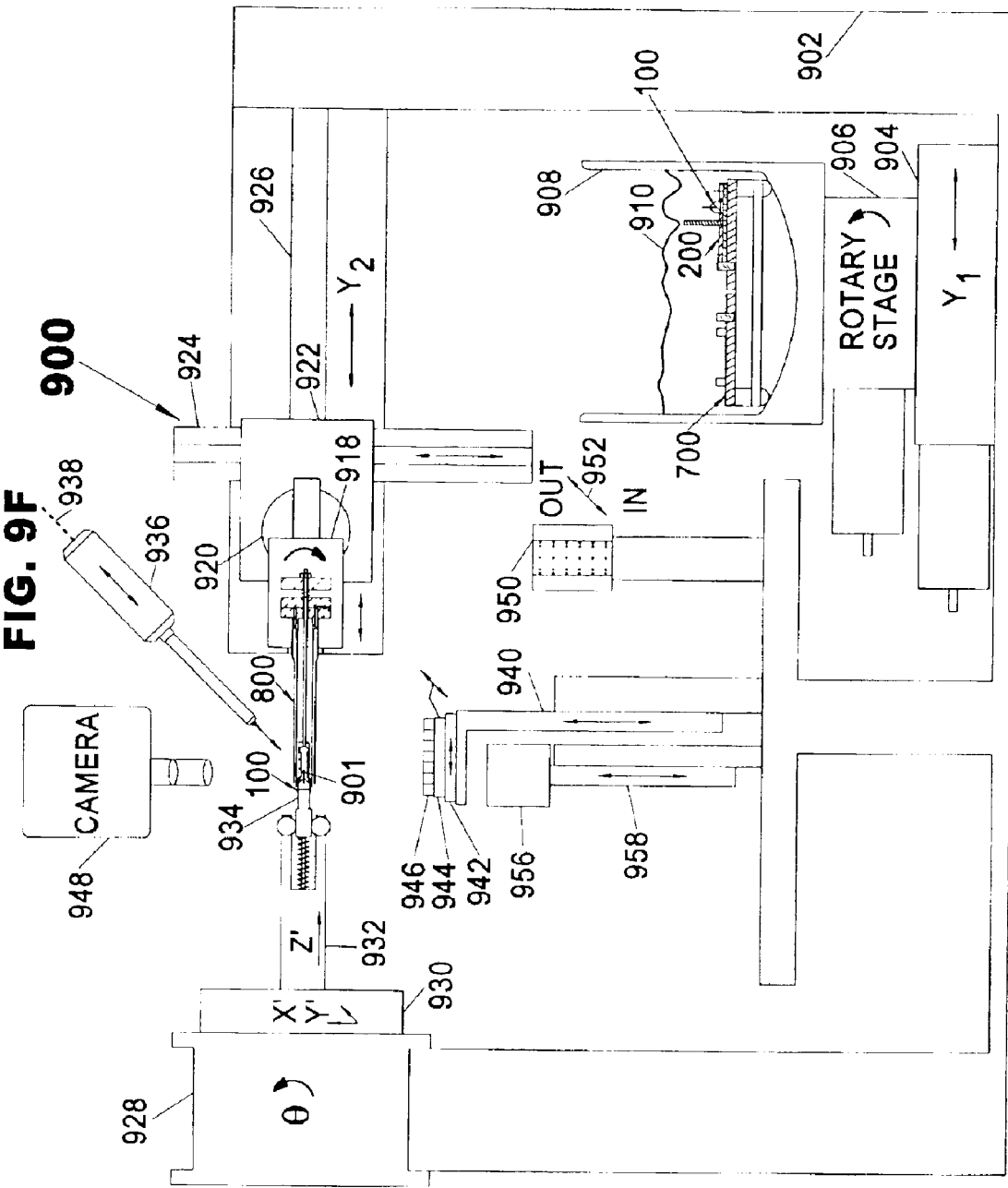
FIG. 9F is a partial front view of the integrated robotic crystal mounting and alignment system showing most of the major subsystems, where the SmallMove stage has moved the sample gripper a short horizontal translation to place the sample assembly in contact with the mounting post of the sample positioner.

Next, in FIG. 9F, the SmallMove 918 pneumatic stage has been extended in a short horizontal translation to mount the sample assembly 100 gently in contact with the magnetically attractive mounting post 934 of the sample positioner. After contact with the mounting post 934 is accomplished, the gripper assembly 800 releases its grip on the sample assembly 100. Now the cryostream unit 936 is actuated along line 938 to approach the sample 110 mounted on the sample assembly 100 mounted on the mounting post 934. The cryostream unit 936 is then activated to cool the sample assembly 100 sample 110 (still cryogenically shielded in the gripper assembly 800) which is now roughly located at a spatial position where the x-ray beam 901 will subsequently irradiate.

Figure 9G:
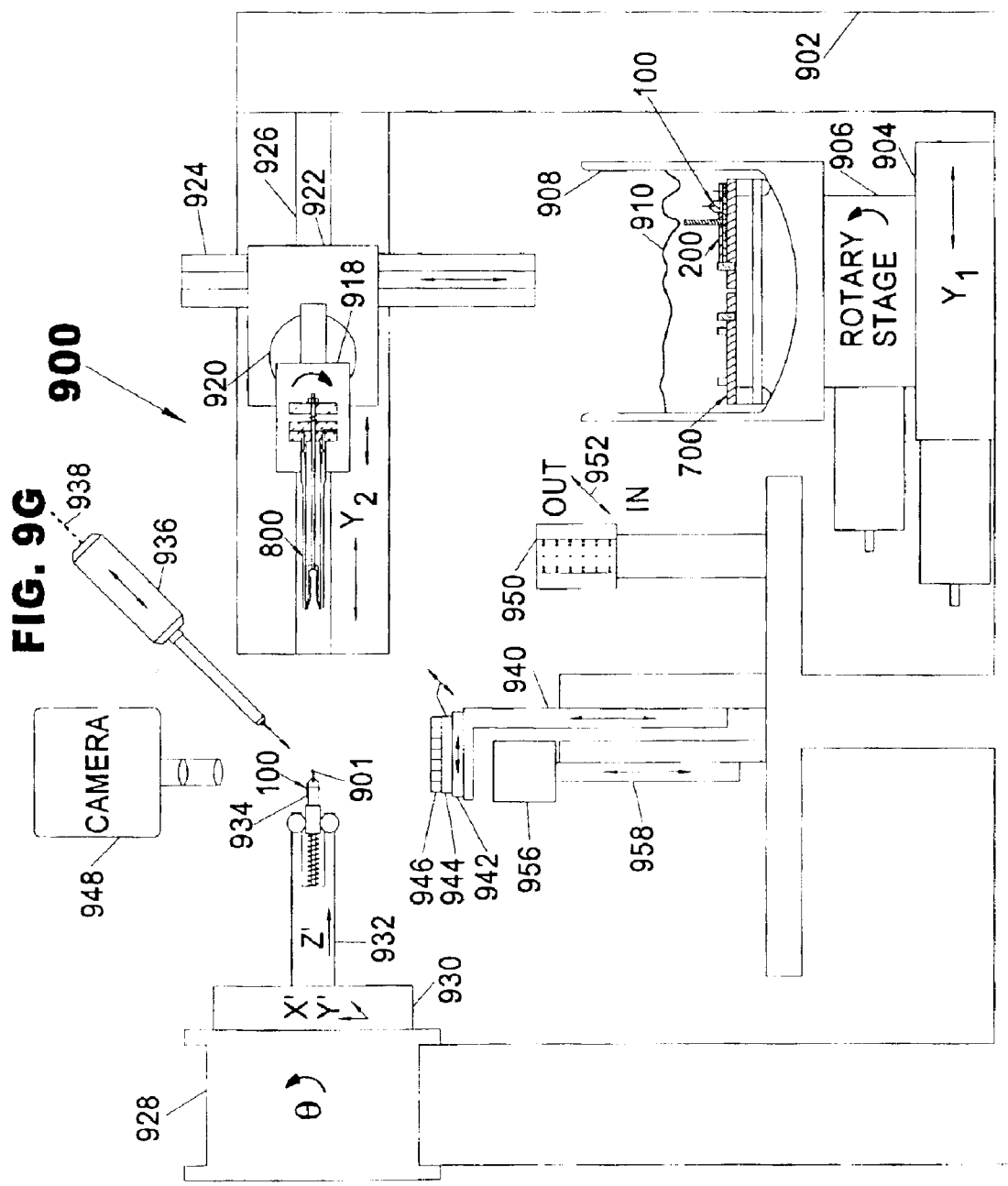
FIG. 9G is a partial front view of the integrated robotic crystal mounting and alignment system showing most of the major subsystems, where the horizontal stage has moved the sample gripper in a long horizontal translation, causing the sample gripper to move to a predetermined distance away from the sample positioner, leaving a sample assembly on the sample positioner mounting post.

Next, in FIG. 9G, the sample gripper 800 has been moved a predetermined distance away from the sample positioner mounting post 934 by the long travel $Y_2$ linear stage, known as the horizontal stage 926. Since the sample gripper 800 has already been released, the sample assembly 100 remains on the sample positioner mounting post 934 due to magnetic attraction. Since the cryostream unit 936 has already been activated, the sample 110 is released from the sample gripper 800 cryogenic interior directly into the cold stream of the cryostream unit 936. In this manner, the sample 110 is never exposed to ambient room temperature.

Initial Sample Reference Position Setup

In this system, a zooming microscopic camera 948 views provides information to correctly position the mounted sample 110 (shown earlier in FIG. 1). In order to establish this spatial position, a three-dimensional position in space must be aligned with the incoming synchrotron x-ray beam 901 while the beam is active. With the x-ray beam 901 active, a pin, or other small axisymmetric alignment shape is moved into the beam until the beam is partially occluded. An x-ray imaging camera, operationally similar to the high resolution macroscopic zooming video camera 948, except that x-rays are detected, and zooming is not likely necessary, is used to image the axisymmetric alignment shape. Either the synchrotron beam current must be greatly reduced, or more preferably the x-ray beam intensity is greatly attenuated by an attenuator to prevent burnout of the camera for this operation.

With the x-ray beam 901 producing an image on the x-ray imaging camera, the axisymmetric alignment shape (typically a small bead, or pin with a point) is moved by coordinated movements of the X' and Y' compound stage 930, and Z' stage 932 axes. Eventually, the movements are manually (or possibly computer controlled) coordinated until the alignment shape enters the field of view of the x-ray imaging camera. By coordinated movements of the X' Y' compound stage 930, and Z' stage 932, and rotation of the goniometer 928, a three-dimensional reference location for the center of the x-ray beam relative to the X' Y' compound stage 930, and Z' stage 932 is developed. Once the alignment shape is aligned to the x-ray beam, the beam may be turned off, or blocked completely, as it is no longer necessary for the initial alignment, as the x-ray beam center relative to the X' Y' compound stage 930, and Z' stage 932 is already known.

The backlighter stage 958 now raises the backlighter 956 so that the alignment shape is back-lit when viewed by the high resolution macroscopic zooming video camera 948. Since the x-ray beam may now be turned off, it is safe for personnel to enter the potentially irradiated hutch area to manually (or by remote control of appropriate tilt or pointing actuators) align the camera 948 to view the alignment shape. Once the camera 948 is correctly positioned to view the alignment shape in roughly the center of field of view, no further camera 948 alignment should be necessary. The camera 948 is then used to view the alignment shape. The alignment shape is viewed, and the pixel location corresponding to the portion of the alignment shape previously positioned in the center of the x-ray beam is recorded. This is the pixel location of the beam center at a particular zoom magnification. The zoom magnification is then increased to a higher magnification so as to more completely fill the field of view of the camera 948, and the pixel location again corresponding to the portion of the alignment shape previously positioned in the center of the x-ray beam is recorded.

Note that the zooming camera 948, can typically only determine position in two dimensions as imaged pixel locations. Typical imaging devices can only focus within a particular optical depth of field, which, depending on the depth of field of the optical image, can provide additional information regarding a distance from the optical objective by either being in or out of focus. In this instance, the zooming camera 948 is preferably parfocally focused on the alignment shape; so that it remains in focus at all zoom magnifications.

Note that, at this time, there are two reference positions being used: the software pixel location of the sample as viewed by the zooming camera 948, which is a two dimensional pixel reference position related to the field of view of the zooming camera 948; and the spatial center of the alignment shape relative to the positioner, a three dimensional reference. These software pixel locations, and the spatial position of the alignment shape relative to the positioner which has previously be collocated through the center of the x-ray beam, are subsequently used to rapidly align samples for x-ray crystallography.

Sample Position Setup

Once the sample assembly 100 has been positioned on the positioner as depicted in FIG. 9G, the sample 110 must be aligned to be concentric with the x-ray beam 901 when it is activated. The previously obtained software pixel locations (two dimensional information) and the spatial center of the alignment shape relative to the positioner (three dimensional information) are used to correctly center the sample crystal 110 for x-ray crystallography. These coordinates are cooperatively used to position the sample crystal 110 relative to the positioner so that the sample crystal 110 may be rotated about the point where the x-ray beam 901 passes when it is activated.

In this system, a zooming microscopic camera 948 initially views the sample 100 (shown earlier in FIG. 1) at minimum magnification, and produces video images of the mounted sample crystal 110. The images are read by a video frame-grabber to provide a digital image of the sample. By either manual or computer algorithmic operation, the frame pixel coordinates of the center of the sample may be determined. The sample positioner (comprised of X' Y' compound stage 930, Z' stage 932, and the goniometer 928) is then actuated to translate the sample 110 to the software reference pixel location arrived at during initial zooming camera 948 alignment in a plane roughly (preferably within 45°, more preferably within 30°, yet more preferably within 15°, and most preferably within 5°) parallel to the image plane of the camera 948. The sample positioner then rotates the sample 110 through angular movement of the goniometer 928, and the process is repeated. At each rotation, the translational increments of the X' and Y' compound stage 930, and Z' stage 932 axes are recorded. Subsequently, these coordinates are used to arrive at the true three-dimensional spatial center of the sample 110 crystal relative to the positioner. The entire process is then optionally repeated at higher zoom magnification levels as necessary. This sample 110 spatial center may be determined relative to the positioner in as few as two rotations due to the short depth of field of the camera 948 at maximum zoom.

The distance from the alignment shape center to the sample 110 center forms an offset vector. The offset vector is used to coordinate the movement of the sample 110 by relative movements of the X' Y' compound stage 930, and Z' stage 932 at each rotation. In this manner, the sample 110 may be rotated in space through a point collocated with the center of the x-ray beam 901 when it is operated. The x-ray beam 901 is not allowed to strike the sample 110 during alignment, so as to minimize any synchrotron-produced x-ray 901 heating or x-ray induced chemical degradation.

Sample X-ray Crystallography

In the normal operation of the system, the sample positioner is moved so that the sample 110 is positioned to a location where synchrotron generated x-rays 901 will be emitted after sample 110 alignment. After the sample 110 is aligned as described above, the synchrotron x-ray beam 901 is unblocked, allowing x-rays to irradiate the sample 110, which can then be rotated to any arbitrary angular position while remaining centered within the x-rays beam 901. After x-ray crystallography is complete, the synchrotron x-ray 901 source is again blocked or shuttered so as to interrupt delivery of the x-ray beam, effectively turning off the x-ray beam. This blocking and unblocking of the x-ray source is important since the x-rays can induce damage to the crystalline sample, thereby degrading the data collected.

Sample Dismounting

Following the FIGS. 9G–9A in reverse is essentially the sequence of motions used by the unmounting protocol, where the sample assembly 100 initially mounted on the sample positioner mounting post 934 is finally replaced in the storage Dewar 908.

For the remaining sample assemblies 100, the sequence of steps previously described is performed in reverse, from 9G (the present data collection state), to 9F, 9E, 9D, 9C, 9B, and 9A where the sample assembly 100 is replace in the Dewar 908. The sample gripper 800 is retracted sufficiently to clear the sample assemblies 100, but still partially immersed in the liquid nitrogen 910. The $Y_1$, linear stage 904 and rotary stage 906 are actuated to position the next sample assembly 100 beneath the sample gripper 800. At this point, the process repeats for sampling of the remaining sample assemblies 100.

After a period of use, the sample gripper 800 may become frost covered. A warm up or defrost protocol is used to remove any accumulated frost from the sample gripper 800. Although the spatial configuration for defrosting is not directly shown in any Figure, it is readily visualized. During the defrost cycle, a heater 950 is extended by an In/Out stage 952, and warm dry nitrogen gas is emitted from the heater 950 onto the sample gripper 800, which has previously been moved into position for defrosting.

Conclusion

All publications, patents, and patent applications mentioned in this application are herein incorporated by reference to the same extent as if each individual publication or patent application were each specifically and individually indicated to be incorporated by reference.

The description given here, and best modes of operation of the invention, are not intended to limit the scope of the invention. Many modifications, alternative constructions, and equivalents may be employed without departing from the scope and spirit of the invention. In particular, the sequence of motions used in mounting and demounting sample assemblies 100 may be re-sequenced in a myriad of permutations without deviating from the general goal to be achieved so long as components and subsystems do not destructively interfere with each other.

We claim:

1. A method of positioning a sample at a predetermined point in space comprising:
    establishing a focused video display of a backlit sample with an electronic camera,
    establishing a software reference for a predetermined point in spare through which an x-ray beam passes,
    aligning a cursor to the apparent center of the backlit sample on the video display,
    moving the backlit sample to the software reference point,
    rotating the backlit sample through an axis non-collinear with the x-ray beam,
    repealing said aligning, moving, and repeating sequence until the backlit sample undergoes rotations essentially about the software reference point.

2. The method of positioning a sample at a predetermined point in space of claim 1 further comprising:
    positioning the sample to the predetermined point in space,
    illuminating the sample with x-ray beam photons, and
    imaging a diffraction resulting from the illumination step to produce a diffraction data image at a particular rotation, the diffraction data image stored on a computer.

3. The method of positioning a sample at a predetermined point in space of claim 2 further comprising:
    imaging of the sample at a plurality of rotations to produce a plurality of diffraction data images stored on a computer at each rotational angle.

4. The method of positioning a sample at a predetermined point in space of claim 3 further comprising:
    ceasing the illumination of the sample with x-ray beam photons after the plurality of diffraction data images stored on a computer at each rotational angle has been completed, and
    computing a crystal composition and atomic placement from the plurality of diffraction data images.

5. The method of positioning a sample at a predetermined point in space of claim 3 further comprising:
    cooling the sample at all times to a temperature not in excess of 150° K.

6. The method of positioning a sample at a predetermined point in space of claim 3 further comprising:
    cooling the sample at all times to a temperature not in excess of 80° K.

* * * * *